US008292880B2

(12) United States Patent
Prakash et al.

(10) Patent No.: US 8,292,880 B2
(45) Date of Patent: Oct. 23, 2012

(54) TARGETED COOLING OF DEPLOYABLE MICROWAVE ANTENNA

(75) Inventors: Mani N. Prakash, Boulder, CO (US); Tao Nguyen, San Jose, CA (US); Christopher T. Rusin, Minneapolis, MN (US)

(73) Assignee: Vivant Medical, Inc., Boulder, CO (US)

( * ) Notice: Subject to any disclaimer, the term of this patent is extended or adjusted under 35 U.S.C. 154(b) by 577 days.

(21) Appl. No.: 12/277,951

(22) Filed: Nov. 25, 2008

(65) Prior Publication Data

US 2009/0138005 A1    May 28, 2009

Related U.S. Application Data

(60) Provisional application No. 60/990,350, filed on Nov. 27, 2007.

(51) Int. Cl.
*A61B 18/04* (2006.01)
*A61B 18/18* (2006.01)
*A61N 1/00* (2006.01)

(52) U.S. Cl. .................... 606/33; 606/41; 607/156
(58) Field of Classification Search .............. 600/425, 600/433; 606/33, 41, 50; 607/101
See application file for complete search history.

(56) References Cited

U.S. PATENT DOCUMENTS

| 2,022,065 A | 11/1935 | Wappler |
| 2,031,682 A | 2/1936 | Frederick et al. |
| 2,047,535 A | 7/1936 | Wappler |
| 3,330,278 A | 7/1967 | Santomieri |
| 3,351,463 A | 11/1967 | Rozner et al. |
| 3,516,412 A | 6/1970 | Ackerman |
| 3,598,108 A | 8/1971 | Jamshidi et al. |
| 3,631,363 A | 12/1971 | Miller |
| 3,714,851 A | 2/1973 | Orser |
| 3,753,700 A | 8/1973 | Harrison et al. |
| 3,886,944 A | 6/1975 | Jamshidi |
| 3,890,977 A | 6/1975 | Wilson |
| 4,010,756 A | 3/1977 | DuMont et al. |
| 4,074,718 A | 2/1978 | Morrison, Jr. et al. |
| 4,103,690 A | 8/1978 | Harris |
| 4,274,408 A | 6/1981 | Nimrod |
| 4,311,154 A | 1/1982 | Sterzer et al. |
| 4,341,226 A | 7/1982 | Peters |
| 4,375,220 A | 3/1983 | Matvias |
| 4,397,313 A | 8/1983 | Vaguine |

(Continued)

FOREIGN PATENT DOCUMENTS

DE        390937        3/1924

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Linda Dvorak
*Assistant Examiner* — Brian M Antiskay

(57) ABSTRACT

The present disclosure relates to devices and methods for the treatment of tissue with microwave energy. The devices and methods disclosed herein utilize an antenna assembly which includes an elongate member, an outer conductor, an inner conductor, at least a portion of which is deployable, and a cooling system. The cooling system disclosed herein may significantly curtail any theoretical, or potential negative effects upon the target tissue experienced during the transmission of microwave energy to the antenna assembly due to ohmic heating.

18 Claims, 11 Drawing Sheets

U.S. PATENT DOCUMENTS

| | | | |
|---|---|---|---|
| 4,402,328 A | 9/1983 | Doring | |
| 4,411,266 A | 10/1983 | Cosman | |
| 4,448,198 A | 5/1984 | Turner | |
| 4,462,412 A | 7/1984 | Turner | |
| 4,557,272 A | 12/1985 | Carr | |
| 4,565,200 A | 1/1986 | Cosman | |
| 4,572,190 A | 2/1986 | Azam et al. | |
| 4,576,177 A | 3/1986 | Webster, Jr. | |
| 4,592,356 A | 6/1986 | Gutierrez | |
| 4,595,007 A | 6/1986 | Mericle | |
| 4,608,977 A | 9/1986 | Brown | |
| 4,612,940 A | 9/1986 | Kasevich et al. | |
| 4,616,656 A | 10/1986 | Nicholson et al. | |
| 4,621,642 A | 11/1986 | Chen | |
| 4,633,880 A | 1/1987 | Osypka et al. | |
| 4,658,836 A | 4/1987 | Turner | |
| 4,662,383 A | 5/1987 | Sogawa et al. | |
| 4,665,906 A | 5/1987 | Jervis | |
| 4,682,606 A | 7/1987 | DeCaprio | |
| 4,700,716 A | 10/1987 | Kasevich et al. | |
| 4,739,759 A | 4/1988 | Rexroth et al. | |
| 4,776,086 A | 10/1988 | Kasevich et al. | |
| 4,798,215 A | 1/1989 | Turner | |
| 4,799,495 A | 1/1989 | Hawkins et al. | |
| 4,800,899 A | 1/1989 | Elliott | |
| 4,825,880 A | 5/1989 | Stauffer et al. | |
| 4,832,024 A | 5/1989 | Boussignac et al. | |
| 4,869,259 A | 9/1989 | Elkins | |
| 4,880,719 A | 11/1989 | Murofushi et al. | |
| 4,925,445 A | 5/1990 | Sakamoto et al. | |
| 4,961,435 A | 10/1990 | Kitagawa et al. | |
| 4,966,583 A | 10/1990 | Debbas | |
| 4,966,597 A | 10/1990 | Cosman | |
| 4,993,430 A | 2/1991 | Shimoyama et al. | |
| 5,011,473 A | 4/1991 | Gatturna | |
| 5,018,530 A | 5/1991 | Rank et al. | |
| 5,029,588 A | 7/1991 | Yock et al. | |
| 5,059,197 A | 10/1991 | Urie et al. | |
| 5,067,957 A | 11/1991 | Jervis | |
| 5,085,659 A | 2/1992 | Rydell | |
| 5,097,844 A | 3/1992 | Turner | |
| 5,103,804 A | 4/1992 | Abele et al. | |
| 5,122,136 A | 6/1992 | Guglielmi et al. | |
| 5,158,084 A | 10/1992 | Ghiatas | |
| 5,171,255 A | 12/1992 | Rydell | |
| 5,183,463 A | 2/1993 | Debbas | |
| 5,190,054 A | 3/1993 | Fetter et al. | |
| 5,190,546 A | 3/1993 | Jervis | |
| 5,197,482 A | 3/1993 | Rank et al. | |
| 5,205,829 A | 4/1993 | Lituchy | |
| 5,217,027 A | 6/1993 | Hermens | |
| 5,221,269 A | 6/1993 | Miller et al. | |
| 5,225,741 A | 7/1993 | Auld et al. | |
| 5,230,623 A | 7/1993 | Guthrie et al. | |
| 5,233,515 A | 8/1993 | Cosman | |
| 5,246,438 A | 9/1993 | Langberg | |
| 5,249,585 A | 10/1993 | Turner et al. | |
| 5,267,994 A | 12/1993 | Gentelia et al. | |
| 5,281,213 A | 1/1994 | Milder et al. | |
| 5,282,845 A | 2/1994 | Bush et al. | |
| 5,300,068 A | 4/1994 | Rosar et al. | |
| 5,301,682 A | 4/1994 | Debbas | |
| 5,314,466 A | 5/1994 | Stern et al. | |
| 5,323,778 A | 6/1994 | Kandarpa et al. | |
| 5,330,470 A | 7/1994 | Hagen | |
| 5,330,518 A | 7/1994 | Neilson et al. | |
| 5,334,193 A | 8/1994 | Nardella | |
| 5,342,357 A | 8/1994 | Nardella | |
| 5,344,441 A | 9/1994 | Gronauer | |
| 5,348,554 A | 9/1994 | Imran et al. | |
| 5,350,419 A | 9/1994 | Bendel et al. | |
| 5,353,804 A | 10/1994 | Kornberg et al. | |
| 5,370,644 A | 12/1994 | Langberg | |
| 5,370,675 A | 12/1994 | Edwards et al. | |
| 5,370,676 A | 12/1994 | Sozanski et al. | |
| 5,383,876 A | 1/1995 | Nardella | |
| 5,383,917 A | 1/1995 | Desai et al. | |
| 5,385,148 A | 1/1995 | Lesh et al. | |
| 5,403,311 A | 4/1995 | Abele et al. | |
| 5,405,346 A | 4/1995 | Grundy et al. | |
| 5,409,000 A | 4/1995 | Imran | |
| 5,409,004 A | 4/1995 | Sloan | |
| 5,409,006 A | 4/1995 | Buchholtz et al. | |
| 5,417,210 A | 5/1995 | Funda et al. | |
| 5,417,686 A | 5/1995 | Peterson et al. | |
| 5,433,739 A | 7/1995 | Sluijter et al. | |
| 5,437,662 A | 8/1995 | Nardella | |
| 5,458,597 A | 10/1995 | Edwards et al. | |
| 5,462,062 A | 10/1995 | Rubinstein et al. | |
| 5,462,521 A | 10/1995 | Brucker et al. | |
| 5,470,308 A | 11/1995 | Edwards et al. | |
| 5,472,441 A | 12/1995 | Edwards et al. | |
| 5,486,183 A | 1/1996 | Middleman et al. | |
| 5,488,958 A | 2/1996 | Topel et al. | |
| 5,490,850 A | 2/1996 | Ellman et al. | |
| 5,500,012 A | 3/1996 | Brucker et al. | |
| 5,507,743 A | 4/1996 | Edwards et al. | |
| 5,520,684 A | 5/1996 | Imran | |
| 5,536,267 A | 7/1996 | Edwards et al. | |
| 5,540,683 A | 7/1996 | Ichikawa et al. | |
| 5,549,644 A * | 8/1996 | Lundquist et al. | 604/22 |
| 5,556,377 A | 9/1996 | Rosen et al. | |
| 5,556,410 A | 9/1996 | Mittermeir et al. | |
| 5,558,673 A | 9/1996 | Edwards et al. | |
| 5,571,147 A | 11/1996 | Sluijter et al. | |
| 5,578,030 A | 11/1996 | Levin | |
| 5,588,432 A | 12/1996 | Crowley | |
| 5,599,294 A | 2/1997 | Edwards et al. | |
| 5,599,295 A | 2/1997 | Rosen et al. | |
| 5,599,345 A | 2/1997 | Edwards et al. | |
| 5,599,346 A | 2/1997 | Edwards et al. | |
| 5,607,389 A | 3/1997 | Edwards et al. | |
| 5,643,197 A | 7/1997 | Brucker et al. | |
| 5,647,871 A | 7/1997 | Levine et al. | |
| 5,662,111 A | 9/1997 | Cosman | |
| 5,672,173 A | 9/1997 | Gough et al. | |
| 5,672,174 A | 9/1997 | Gough et al. | |
| 5,683,384 A | 11/1997 | Gough et al. | |
| 5,685,853 A | 11/1997 | Bonnet | |
| 5,688,267 A | 11/1997 | Panescu et al. | |
| 5,700,243 A | 12/1997 | Narciso, Jr. | |
| 5,709,697 A | 1/1998 | Ratcliff et al. | |
| 5,720,718 A | 2/1998 | Rosen et al. | |
| 5,735,847 A | 4/1998 | Gough et al. | |
| 5,741,225 A | 4/1998 | Lax et al. | |
| 5,749,887 A | 5/1998 | Heske et al. | |
| 5,775,338 A | 7/1998 | Hastings | |
| 5,776,176 A | 7/1998 | Rudie | |
| 5,792,146 A | 8/1998 | Cosman | |
| 5,794,626 A | 8/1998 | Kieturakis | |
| 5,795,308 A | 8/1998 | Russin | |
| 5,800,484 A | 9/1998 | Gough et al. | |
| 5,800,486 A | 9/1998 | Thome et al. | |
| 5,807,339 A | 9/1998 | Bostrom et al. | |
| 5,810,804 A | 9/1998 | Gough et al. | |
| 5,848,967 A | 12/1998 | Cosman | |
| 5,849,011 A | 12/1998 | Jones et al. | |
| 5,853,366 A | 12/1998 | Dowlatshahi | |
| 5,855,576 A | 1/1999 | LeVeen et al. | |
| 5,861,002 A | 1/1999 | Desai | |
| 5,863,290 A | 1/1999 | Gough et al. | |
| 5,868,740 A | 2/1999 | LeVeen et al. | |
| 5,871,523 A | 2/1999 | Fleischman et al. | |
| 5,879,357 A | 3/1999 | Heaton et al. | |
| 5,882,316 A | 3/1999 | Chu et al. | |
| 5,897,554 A | 4/1999 | Chia et al. | |
| 5,902,310 A | 5/1999 | Foerster et al. | |
| 5,904,690 A | 5/1999 | Middleman et al. | |
| 5,904,691 A | 5/1999 | Barnett et al. | |
| 5,904,709 A | 5/1999 | Arndt et al. | |
| 5,921,982 A | 7/1999 | Lesh et al. | |
| 5,938,692 A | 8/1999 | Rudie | |
| 5,941,890 A | 8/1999 | Voegele et al. | |
| 5,943,719 A | 8/1999 | Feldman et al. | |
| 5,951,546 A | 9/1999 | Lorentzen | |
| 5,954,655 A | 9/1999 | Hussman | |
| 5,954,719 A | 9/1999 | Chen et al. | |

| Patent | Date | Inventor |
|---|---|---|
| 5,957,969 A | 9/1999 | Warner et al. |
| 5,974,343 A | 10/1999 | Brevard et al. |
| 5,980,563 A | 11/1999 | Tu et al. |
| 5,989,265 A | 11/1999 | Bouquet De La Joliniere et al. |
| 6,001,093 A | 12/1999 | Swanson et al. |
| 6,006,126 A | 12/1999 | Cosman |
| 6,007,495 A | 12/1999 | Matula |
| 6,016,811 A | 1/2000 | Knopp et al. |
| 6,019,757 A | 2/2000 | Scheldrup |
| 6,022,362 A | 2/2000 | Lee et al. |
| 6,026,331 A | 2/2000 | Feldberg et al. |
| 6,027,501 A | 2/2000 | Goble et al. |
| 6,027,524 A | 2/2000 | Petit |
| 6,031,375 A | 2/2000 | Atalar et al. |
| 6,032,078 A | 2/2000 | Rudie |
| 6,039,735 A | 3/2000 | Greep |
| 6,050,954 A | 4/2000 | Mittermeier |
| 6,051,008 A | 4/2000 | Saadat et al. |
| 6,053,876 A | 4/2000 | Fisher |
| 6,053,912 A | 4/2000 | Panescu et al. |
| 6,053,925 A | 4/2000 | Barnhart |
| 6,056,744 A | 5/2000 | Edwards |
| 6,059,780 A | 5/2000 | Gough et al. |
| 6,061,551 A | 5/2000 | Sorrells et al. |
| 6,073,051 A | 6/2000 | Sharkey et al. |
| 6,074,389 A | 6/2000 | Levine et al. |
| 6,080,113 A | 6/2000 | Heneveld et al. |
| 6,080,114 A | 6/2000 | Russin |
| 6,080,149 A | 6/2000 | Huang et al. |
| 6,080,150 A | 6/2000 | Gough |
| 6,097,985 A | 8/2000 | Kasevich et al. |
| 6,106,518 A | 8/2000 | Wittenberger et al. |
| 6,106,524 A | 8/2000 | Eggers et al. |
| 6,122,551 A | 9/2000 | Rudie et al. |
| 6,132,426 A | 10/2000 | Kroll |
| 6,134,476 A | 10/2000 | Arndt et al. |
| 6,146,378 A | 11/2000 | Mikus et al. |
| 6,146,379 A | 11/2000 | Fleischman et al. |
| 6,146,380 A | 11/2000 | Racz et al. |
| 6,146,657 A | 11/2000 | Unger et al. |
| 6,162,216 A | 12/2000 | Guziak et al. |
| 6,176,856 B1 | 1/2001 | Jandak et al. |
| 6,178,354 B1 | 1/2001 | Gibson |
| 6,181,970 B1 | 1/2001 | Kasevich |
| 6,203,541 B1 | 3/2001 | Keppel |
| 6,217,528 B1 | 4/2001 | Koblish et al. |
| 6,223,086 B1 | 4/2001 | Carl et al. |
| 6,230,060 B1 | 5/2001 | Mawhinney |
| 6,233,490 B1 | 5/2001 | Kasevich |
| 6,241,725 B1 | 6/2001 | Cosman |
| 6,245,064 B1 | 6/2001 | Lesh et al. |
| 6,245,318 B1 | 6/2001 | Klibanov et al. |
| 6,246,912 B1 | 6/2001 | Sluijter et al. |
| 6,251,128 B1 | 6/2001 | Knopp et al. |
| 6,275,738 B1 | 8/2001 | Kasevich et al. |
| 6,277,113 B1 | 8/2001 | Berube |
| 6,287,305 B1 | 9/2001 | Heim et al. |
| 6,290,715 B1 | 9/2001 | Sharkey et al. |
| 6,306,132 B1 | 10/2001 | Moorman et al. |
| 6,308,091 B1 | 10/2001 | Avitall |
| 6,325,796 B1 | 12/2001 | Berube et al. |
| 6,330,479 B1 | 12/2001 | Stauffer |
| 6,337,998 B1 | 1/2002 | Behl et al. |
| 6,346,104 B2 | 2/2002 | Daly et al. |
| 6,347,251 B1 | 2/2002 | Deng |
| 6,355,033 B1 | 3/2002 | Moorman et al. |
| 6,375,606 B1 | 4/2002 | Garibaldi et al. |
| 6,405,733 B1 | 6/2002 | Fogarty et al. |
| 6,432,070 B1 | 8/2002 | Talish et al. |
| 6,471,696 B1 | 10/2002 | Berube et al. |
| 6,478,793 B1 | 11/2002 | Cosman et al. |
| 6,496,738 B2 | 12/2002 | Carr |
| 6,500,172 B1 | 12/2002 | Panescu et al. |
| 6,506,189 B1 | 1/2003 | Rittamn et al. |
| 6,514,251 B1 | 2/2003 | Ni et al. |
| 6,530,922 B2 | 3/2003 | Cosman et al. |
| 6,564,806 B1 | 5/2003 | Fogarty et al. |
| 6,569,159 B1 | 5/2003 | Edwards et al. |
| 6,575,969 B1 | 6/2003 | Rittman, III et al. |
| 6,582,426 B2 | 6/2003 | Moorman et al. |
| 6,603,994 B2 | 8/2003 | Wallace et al. |
| 6,605,085 B1 | 8/2003 | Edwards |
| 6,613,047 B2 | 9/2003 | Edwards |
| 6,652,520 B2 | 11/2003 | Moorman et al. |
| 6,663,624 B2 * | 12/2003 | Edwards et al. ................ 606/41 |
| 6,685,700 B2 | 2/2004 | Behl et al. |
| 6,685,729 B2 | 2/2004 | Gonzalez |
| 6,699,241 B2 | 3/2004 | Rappaport et al. |
| 6,722,371 B1 | 4/2004 | Bush et al. |
| 6,725,080 B2 | 4/2004 | Melkent et al. |
| 6,752,154 B2 | 6/2004 | Fogarty et al. |
| 6,752,767 B2 | 6/2004 | Turovskiy et al. |
| 6,878,147 B2 | 4/2005 | Prakash et al. |
| 6,918,907 B2 | 7/2005 | Kelly et al. |
| 6,944,504 B1 | 9/2005 | Arndt et al. |
| 6,957,108 B2 | 10/2005 | Turner et al. |
| 6,962,586 B2 | 11/2005 | Berube et al. |
| 6,997,925 B2 | 2/2006 | Maguire et al. |
| 7,001,379 B2 | 2/2006 | Behl et al. |
| 7,025,765 B2 | 4/2006 | Balbierz et al. |
| 7,025,767 B2 | 4/2006 | Schaefer et al. |
| 7,025,768 B2 | 4/2006 | Elliott |
| 7,027,851 B2 | 4/2006 | Mejia |
| 7,027,852 B2 | 4/2006 | Helland |
| 7,041,094 B2 | 5/2006 | Connors et al. |
| 7,063,682 B1 | 6/2006 | Whayne et al. |
| 7,087,851 B2 | 8/2006 | Mayer |
| 7,089,045 B2 | 8/2006 | Fuimaono et al. |
| 7,099,712 B2 | 8/2006 | Fuimaono et al. |
| 7,108,696 B2 | 9/2006 | Daniel et al. |
| 7,113,832 B2 | 9/2006 | Longo |
| 7,137,980 B2 | 11/2006 | Buysse et al. |
| 7,155,270 B2 | 12/2006 | Solis et al. |
| 7,156,842 B2 | 1/2007 | Sartor et al. |
| 7,156,845 B2 | 1/2007 | Mulier et al. |
| 7,160,292 B2 | 1/2007 | Moorman et al. |
| 7,160,296 B2 | 1/2007 | Pearson et al. |
| 7,179,255 B2 | 2/2007 | Lettice et al. |
| 7,179,522 B2 | 2/2007 | Hiel et al. |
| 7,186,222 B1 | 3/2007 | Callister et al. |
| 7,186,251 B2 | 3/2007 | Malecki et al. |
| 7,187,963 B2 | 3/2007 | Coleman et al. |
| 7,195,629 B2 | 3/2007 | Behl et al. |
| 7,195,630 B2 | 3/2007 | Ciarrocca |
| 7,197,349 B2 | 3/2007 | Taimisto et al. |
| 7,197,363 B2 | 3/2007 | Prakash et al. |
| 7,200,445 B2 | 4/2007 | Dalbec et al. |
| 7,207,989 B2 | 4/2007 | Pike, Jr. et al. |
| 7,218,958 B2 | 5/2007 | Rashidi |
| 7,220,259 B2 | 5/2007 | Harrington et al. |
| 7,226,444 B1 | 6/2007 | Ellman et al. |
| 7,226,446 B1 | 6/2007 | Mody et al. |
| 7,228,164 B2 | 6/2007 | Fuimaono et al. |
| 7,229,418 B2 | 6/2007 | Burbank et al. |
| 7,229,438 B2 | 6/2007 | Young |
| 7,235,070 B2 | 6/2007 | Vanney |
| 7,235,073 B2 | 6/2007 | Levine et al. |
| 7,238,184 B2 | 7/2007 | Megerman et al. |
| 7,252,665 B2 | 8/2007 | Starkebaum et al. |
| 7,257,434 B2 | 8/2007 | Fuimaono et al. |
| 7,257,435 B2 | 8/2007 | Plaza |
| 7,258,690 B2 | 8/2007 | Sutton et al. |
| 7,261,711 B2 | 8/2007 | Mulier et al. |
| 7,261,712 B2 | 8/2007 | Burbank et al. |
| 7,264,619 B2 | 9/2007 | Venturelli |
| 7,267,683 B2 | 9/2007 | Sharkey et al. |
| 7,274,957 B2 | 9/2007 | Drysen |
| 7,276,064 B2 | 10/2007 | Paul et al. |
| 7,278,991 B2 | 10/2007 | Morris et al. |
| 7,282,049 B2 | 10/2007 | Orszulak et al. |
| 7,282,050 B2 | 10/2007 | Starkebaum et al. |
| 7,282,051 B2 | 10/2007 | Rioux et al. |
| 7,282,061 B2 | 10/2007 | Sharkey et al. |
| 7,285,119 B2 | 10/2007 | Stewart et al. |
| 7,294,125 B2 | 11/2007 | Phalen et al. |
| 7,294,127 B2 | 11/2007 | Leung et al. |
| 7,294,143 B2 | 11/2007 | Francischelli |
| 7,302,285 B2 | 11/2007 | Fuimaono et al. |

| Patent Number | Date | Inventor |
|---|---|---|
| 7,303,558 B2 | 12/2007 | Swanson |
| 7,306,591 B2 | 12/2007 | Thomas et al. |
| 7,306,595 B2 | 12/2007 | Ostrovsky et al. |
| 7,311,703 B2 * | 12/2007 | Turovskiy et al. .............. 606/33 |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,326,201 B2 | 2/2008 | Fjield et al. |
| 7,326,208 B2 | 2/2008 | Vanney et al. |
| 7,329,253 B2 | 2/2008 | Brounstein et al. |
| 7,331,947 B2 | 2/2008 | McGuckin, Jr. et al. |
| 7,331,959 B2 | 2/2008 | Cao et al. |
| 7,331,960 B2 | 2/2008 | Schaer |
| 7,335,196 B2 | 2/2008 | Swanson et al. |
| 7,335,197 B2 | 2/2008 | Sage et al. |
| 7,335,198 B2 | 2/2008 | Eggers et al. |
| RE40,156 E | 3/2008 | Sharps et al. |
| 7,341,586 B2 | 3/2008 | Daniel et al. |
| 7,344,533 B2 | 3/2008 | Pearson et al. |
| 7,354,436 B2 | 4/2008 | Rioux et al. |
| 7,357,801 B2 | 4/2008 | Burbank et al. |
| 7,364,578 B2 | 4/2008 | Francischelli et al. |
| 7,364,579 B2 | 4/2008 | Mulier et al. |
| 7,367,974 B2 | 5/2008 | Haemmerich et al. |
| 7,367,975 B2 | 5/2008 | Malecki et al. |
| 7,371,234 B2 | 5/2008 | Young |
| 7,387,625 B2 | 6/2008 | Hovda et al. |
| 7,387,626 B2 | 6/2008 | Edwards et al. |
| 7,387,628 B1 | 6/2008 | Behl et al. |
| 7,387,631 B2 | 6/2008 | Durgin et al. |
| 7,392,077 B2 | 6/2008 | Mueller et al. |
| 7,396,355 B2 | 7/2008 | Goldman et al. |
| 7,399,299 B2 | 7/2008 | Daniel et al. |
| 7,400,930 B2 | 7/2008 | Sharkey et al. |
| 7,406,970 B2 | 8/2008 | Zikorus et al. |
| 7,410,486 B2 | 8/2008 | Fuimaono et al. |
| 7,412,274 B2 | 8/2008 | Mejia |
| 7,416,549 B2 | 8/2008 | Young et al. |
| 7,419,486 B2 | 9/2008 | Kampa |
| 7,419,487 B2 | 9/2008 | Johnson et al. |
| 7,419,488 B2 | 9/2008 | Ciarrocca et al. |
| 7,419,489 B2 | 9/2008 | Vanney et al. |
| 7,422,563 B2 | 9/2008 | Boschak et al. |
| 7,422,583 B2 | 9/2008 | Maurice |
| 7,422,587 B2 | 9/2008 | Bek et al. |
| 7,425,212 B1 | 9/2008 | Danek et al. |
| 7,439,736 B2 | 10/2008 | Meaney et al. |
| 7,467,015 B2 | 12/2008 | Van der Weide |
| 7,480,533 B2 | 1/2009 | Cosman et al. |
| 7,565,207 B2 | 7/2009 | Turner et al. |
| 2001/0001819 A1 | 5/2001 | Lee et al. |
| 2001/0034518 A1 | 10/2001 | Edwards et al. |
| 2001/0037812 A1 | 11/2001 | Dobak, III et al. |
| 2001/0051131 A1 | 12/2001 | Unger |
| 2002/0022832 A1 | 2/2002 | Mikus et al. |
| 2002/0022836 A1 | 2/2002 | Goble et al. |
| 2002/0058933 A1 | 5/2002 | Christopherson et al. |
| 2002/0059938 A1 | 5/2002 | Fogarty et al. |
| 2002/0072742 A1 | 6/2002 | Schaefer et al. |
| 2002/0087151 A1 | 7/2002 | Mody et al. |
| 2002/0111615 A1 | 8/2002 | Cosman et al. |
| 2002/0120261 A1 | 8/2002 | Morris et al. |
| 2002/0133148 A1 | 9/2002 | Daniel et al. |
| 2002/0147444 A1 | 10/2002 | Shah et al. |
| 2002/0156472 A1 | 10/2002 | Lee et al. |
| 2002/0198520 A1 | 12/2002 | Coen et al. |
| 2003/0004506 A1 | 1/2003 | Messing |
| 2003/0018247 A1 | 1/2003 | Gonzalez |
| 2003/0065317 A1 | 4/2003 | Rudie et al. |
| 2003/0069578 A1 | 4/2003 | Hall et al. |
| 2003/0088242 A1 | 5/2003 | Prakash et al. |
| 2003/0109862 A1 | 6/2003 | Prakash et al. |
| 2003/0195499 A1 | 10/2003 | Prakash et al. |
| 2003/0195500 A1 | 10/2003 | Moorman et al. |
| 2003/0208199 A1 | 11/2003 | Keane |
| 2004/0002745 A1 | 1/2004 | Fleming et al. |
| 2004/0039429 A1 | 2/2004 | Daniel et al. |
| 2004/0097805 A1 | 5/2004 | Verard et al. |
| 2004/0168692 A1 | 9/2004 | Fogarty et al. |
| 2004/0181216 A1 | 9/2004 | Kelly et al. |
| 2004/0199161 A1 | 10/2004 | Truckai et al. |
| 2004/0225286 A1 | 11/2004 | Elliott |
| 2004/0242992 A1 | 12/2004 | Hareyama |
| 2004/0254573 A1 | 12/2004 | Dycus |
| 2004/0267156 A1 | 12/2004 | Turovskiy et al. |
| 2004/0267256 A1 | 12/2004 | Garabedian et al. |
| 2005/0062666 A1 | 3/2005 | Prakash et al. |
| 2005/0070895 A1 | 3/2005 | Ryan et al. |
| 2005/0085881 A1 | 4/2005 | Prakash et al. |
| 2005/0096681 A1 | 5/2005 | Desinger et al. |
| 2005/0107784 A1 | 5/2005 | Moses |
| 2005/0107785 A1 | 5/2005 | Dycus |
| 2005/0113824 A1 | 5/2005 | Sartor et al. |
| 2005/0119655 A1 | 6/2005 | Moses |
| 2005/0154387 A1 | 7/2005 | Moses |
| 2005/0155743 A1 | 7/2005 | Getz, Jr. et al. |
| 2006/0079885 A1 | 4/2006 | Rick et al. |
| 2006/0079887 A1 | 4/2006 | Buysse |
| 2006/0217702 A1 | 9/2006 | Young |
| 2007/0046260 A1 | 3/2007 | Ishikawa |
| 2007/0049921 A1 | 3/2007 | Konishi et al. |
| 2007/0066971 A1 | 3/2007 | Podhajsky |
| 2007/0073285 A1 | 3/2007 | Peterson |
| 2007/0078453 A1 | 4/2007 | Johnson |
| 2007/0078454 A1 | 4/2007 | McPherson |
| 2007/0100405 A1 | 5/2007 | Thompson et al. |
| 2007/0118110 A1 | 5/2007 | Girard et al. |
| 2007/0129710 A1 | 6/2007 | Rudko et al. |
| 2007/0129721 A1 | 6/2007 | Phan et al. |
| 2007/0135700 A1 | 6/2007 | Taimisto et al. |
| 2007/0149963 A1 | 6/2007 | Matsukuma et al. |
| 2007/0149966 A1 | 6/2007 | Dahla et al. |
| 2007/0161977 A1 | 7/2007 | Moorman et al. |
| 2007/0179491 A1 | 8/2007 | Kratoska et al. |
| 2007/0179494 A1 | 8/2007 | Faure |
| 2007/0179496 A1 | 8/2007 | Swoyer et al. |
| 2007/0185483 A1 | 8/2007 | Butty et al. |
| 2007/0198006 A1 | 8/2007 | Prakash et al. |
| 2007/0203480 A1 | 8/2007 | Mody et al. |
| 2007/0203486 A1 | 8/2007 | Young |
| 2007/0219546 A1 | 9/2007 | Mody et al. |
| 2007/0232871 A1 | 10/2007 | Sinofsky et al. |
| 2007/0258838 A1 | 11/2007 | Drake et al. |
| 2007/0260234 A1 | 11/2007 | McCullagh et al. |
| 2007/0260240 A1 | 11/2007 | Rusin |
| 2007/0265609 A1 | 11/2007 | Thapliyal et al. |
| 2007/0265610 A1 | 11/2007 | Thapliyal et al. |
| 2007/0270789 A1 | 11/2007 | Berger |
| 2007/0270794 A1 | 11/2007 | Anderson et al. |
| 2007/0287996 A1 | 12/2007 | Rioux |
| 2007/0287999 A1 | 12/2007 | Malecki et al. |
| 2007/0293856 A1 | 12/2007 | Paul et al. |
| 2007/0299434 A1 | 12/2007 | Malecki et al. |
| 2007/0299435 A1 | 12/2007 | Crowe et al. |
| 2008/0004615 A1 | 1/2008 | Woloszko et al. |
| 2008/0021448 A1 | 1/2008 | Orszulak |
| 2008/0027424 A1 | 1/2008 | DeCarlo et al. |
| 2008/0183165 A1 | 7/2008 | Buysse et al. |
| 2008/0287946 A1 | 11/2008 | DeCarlo et al. |
| 2008/0319438 A1 | 12/2008 | DeCarlo |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 2407559 | 2/1974 |
| DE | 2429021 | 1/1976 |
| DE | 3711511 | 6/1988 |
| DE | 4339049 | 5/1995 |
| DE | 19848540 | 5/2000 |
| DE | 10224154 | 12/2003 |
| DE | 102004022206 | 12/2005 |
| DE | 202005015147 | 3/2006 |
| EP | 0171967 A | 2/1986 |
| EP | 0246350 | 11/1987 |
| EP | 0310431 | 4/1989 |
| EP | 0 385 604 A2 | 9/1990 |
| EP | 0 395 997 A1 | 11/1990 |

| | | |
|---|---|---|
| EP | 0 481 685 A1 | 4/1992 |
| EP | 0 556 705 | 8/1993 |
| EP | 0 558 429 | 9/1993 |
| EP | 0 608 609 | 8/1994 |
| EP | 0 667 126 A1 | 8/1995 |
| EP | 0 829 232 A2 | 3/1998 |
| EP | 0 908 154 A1 | 4/1999 |
| EP | 0 908 156 A1 | 4/1999 |
| EP | 1 070 518 A2 | 1/2001 |
| EP | 1 278 007 | 1/2003 |
| EP | 1 465 037 A | 10/2004 |
| EP | 1 559 377 A1 | 8/2005 |
| EP | 1 645 234 | 4/2006 |
| EP | 1 656 900 | 5/2006 |
| EP | 1 810 627 | 7/2007 |
| FR | 1 275 415 | 9/1960 |
| FR | 2 276 027 | 6/1974 |
| FR | 2862813 | 5/2005 |
| FR | 2864439 | 7/2005 |
| WO | WO 88/06864 A1 | 9/1988 |
| WO | WO 92/12678 A1 | 8/1992 |
| WO | WO 93/20767 A1 | 10/1993 |
| WO | WO 93/20768 A1 | 10/1993 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/27328 A1 | 9/1996 |
| WO | WO 96/29946 | 10/1996 |
| WO | WO 96/34571 A1 | 11/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO97/41924 | 11/1997 |
| WO | WO97/43971 | 11/1997 |
| WO | WO 97/48449 A1 | 12/1997 |
| WO | WO 97/48450 A1 | 12/1997 |
| WO | WO 97/48451 A1 | 12/1997 |
| WO | WO 98/06341 A1 | 2/1998 |
| WO | WO 98/30160 A1 | 7/1998 |
| WO | WO 99/01074 | 1/1999 |
| WO | WO 99/04704 A2 | 2/1999 |
| WO | WO 99/04710 | 2/1999 |
| WO | WO 99/22657 | 5/1999 |
| WO | WO 99/25248 A1 | 5/1999 |
| WO | WO 99/43268 A1 | 9/1999 |
| WO | WO 99/44506 A1 | 9/1999 |
| WO | WO 99/44520 A1 | 9/1999 |
| WO | WO 99/56642 A1 | 11/1999 |
| WO | WO 99/56643 A1 | 11/1999 |
| WO | WO 99/56812 A2 | 11/1999 |
| WO | WO 99/58065 A1 | 11/1999 |
| WO | WO 99/66834 A1 | 12/1999 |
| WO | WO 00/10471 A1 | 3/2000 |
| WO | WO 00/12009 A2 | 3/2000 |
| WO | WO 00/12010 A1 | 3/2000 |
| WO | WO 00/13602 A2 | 3/2000 |
| WO | WO 00/16697 A2 | 3/2000 |
| WO | WO 00/24320 A1 | 5/2000 |
| WO | WO 00/28913 A1 | 5/2000 |
| WO | WO 00/30531 A1 | 6/2000 |
| WO | WO 00/33743 A1 | 6/2000 |
| WO | WO00/48672 | 8/2000 |
| WO | WO 00/49957 A1 | 8/2000 |
| WO | WO00/51513 | 9/2000 |
| WO | WO 00/56239 A1 | 9/2000 |
| WO | WO 00/57811 A1 | 10/2000 |
| WO | WO 00/67846 | 11/2000 |
| WO | WO 01/00114 A1 | 1/2001 |
| WO | WO01/01847 | 1/2001 |
| WO | WO 01/05317 A1 | 1/2001 |
| WO | WO 01/05320 A1 | 1/2001 |
| WO | WO 01/60235 A2 | 8/2001 |
| WO | WO01/74252 | 10/2001 |
| WO | WO02/45790 | 6/2002 |
| WO | WO02/061880 | 8/2002 |
| WO | WO 03/034932 A1 | 5/2003 |
| WO | WO 03/039385 A2 | 5/2003 |
| WO | WO 03/088806 A2 | 10/2003 |
| WO | WO 03/088858 A1 | 10/2003 |
| WO | WO 2004/045436 | 6/2004 |
| WO | WO2004/112628 | 12/2004 |
| WO | WO 2005/009528 | 2/2005 |
| WO | WO 2005/011049 A2 | 2/2005 |
| WO | WO2005/016119 | 2/2005 |
| WO | WO 2006/068430 | 6/2006 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Cosman ER, Cosman BJ: "Methods of Making Nervous System Lesions", in William RH, Rengachary SS (eds): Neurosurgery. New York: McGraw-Hill, vol. 111, pp. 2490-2498, 1984.
Anderson, Gary et al., "A numerical study of rapid heating for high temperature radio frequency hyperthermia", International Journal of Bio-Medical Computing, 35 (1994) 297-307.
Goldberg, et al., "Tissue Ablation with Radiofrequency: Effective Probe Size, Gauge, Duration and Temperature and Lesion Volume", Acad Radio, 1995, vol. 2, No. 5, pp. 399-404.
Melvin A. Astrahan, "A Localized Current Field Hyperthermia System for Use with 192-Iridium Interstitial Implants", Medical Physics, 9(3), May/Jun. 1982.
Cosman et al. "Theoretical Aspects of Radiofrequency Lesions in the Dorsal Root Entry Zone". Neurosurgery 15:945-950, 1984.
Stuart W. Young, Nuclear Magnetic Resonance Imaging—Basic Principles, Raven Press, New York, 1984.
E.R. Cosman, et al., "Radiofrequency Lesion Generation and its Effect on Tissue Impedance", Applied Neurophysiology, 51:230-242, 1988.
K. Ogata, Modem Control Engineering, Prentice-Hall, Englewood Cliffs, N.J., 1970.
E. Alexander et al., "Magnetic resonance image-directed stereotactic neurosurgery: use of image fusion with computerized tomography to enhance spatial accuracy", J. Neurosurg., 83:271, 276, 1995.
Reidenbach (1995) "First Experimental Results with Special Applicators for High-Frequency Interstitial Thermotherapy", Society Minimally Ivasive Therapy, 4(Suppl 1) :40 (Abstr).
Organ LW. (1976) "Electrophysiologic Principles of Radiofrequency Lesion Making" Appl. Neurophysiol, vol. 39: pp. 69-76.
Livraghi et al. (1995) "Saline-enhanced RF Tissue Ablation in the Treatment of Liver Metastases", Radiology, 205-210.
Solbiati et al. (1995) "Percutaneous US-guided RF Tissue Ablation of Liver Metastases: Long-term Follow-up", Radiology, 197(P): 199.
Solbiati, et al. (2001) "Percutaneous Radio-frequency Ablation of Hepatic Metastases from Colorectal Cancer: Long-term Results in 117 Patients", *Radiology*, vol. 221, pp. 159-166.
Goldberg, et al., "Image-guided Radiofrequency Tumor Ablation: Challenges and Opportunities—Part I", (2001) *J Vasc. Interv. Radiol*, vol. 12, pp. 1021-1032.
McGahan et al. (1995) "Percutaneous Ultrasound-guided Radiofrequency Electrocautery Ablation of Prostate Tissue in Dogs", Acad Radiol, vol. 2, No. 1:pp. 61-65.
Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

Bulletin of the American Physical Society, vol. 47, No. 5, Aug. 2002.

McRury, et al. (2000) "The Effect of Ablation Sequence and Duration on Lesion Shape Using Rapidly Pulsed Radiofrequency Energy Through Electrodes", Springer Netherlands, vol. 4, No. 1, pp. 307-320.

Anonymous. (1987). Homer Mammalok® Breast Lesion Needle/Wire Localizer, Namic® Angiographic Systems Division, Glens Falls, New York, (Hospital products price list), 4 pages.

Anonymous. (1999). Auto Suture MIBB Site Marker: Single Use Clip Applier, United States Surgical (Product instructions), 2 pages.

Anonymous. (1999). MIBB Site Marker, United States Surgical (Sales brochure), 4 pages.

Anonymous. (2001). Disposable Chiba Biopsy Needles and Trays, Biopsy and Special Purpose Needles Cook Diagnostic and Interventional Products Catalog (Products list), 4 pages.

Chou, C.K. (1995). "Radiofrequency Hyperthermia in Cancer Therapy," Chapter 94 in Biologic Effects of Nonionizing Electromagnetic Fields. CRC Press, Inc. pp. 1424-1428.

Gennari, R. et al. (Jun. 2000). "Use of Technetium-99m-Labeled Colloid Albumin for Preoperative and Intraoperative Localization of Nonpalpable Breast Lesions," J. Am. Coll. Surg. 190(6):692-699.

Kopans, D.B. et al. (Nov. 1985). "Spring Hookwire Breast Lesion Localizer: Use with Rigid-Compression. Mammographic Systems," Radiology 157(2):537-538.

MDTECH product literature. (Mar. 2000). "D Wire": product description, one page.

MDTECH product literature. (Dec. 1999). "FlexStrand": product description, one page.

Mullan, B.F. et al. (May 1999). "Lung Nodules: Improved Wire for CT-Guided Localization," Radiology 211:561-565.

Urrutia et al. (1988). "Retractable-Barb Needle for Breast Lesion Localization: Use in 60 Cases," Radiology 169(3):845-847.

Joseph G. Andriole, M.D., et al., "Biopsy Needle Characteristics Assessed in the Laboratory", Radiology 148: 659-662, Sep. 1983.

T. Matsukawa, et al. "Percutaneous Microwave Coagulation Therapy in Liver Tumors", Acta Radiologica vol. 38, pp. 410-415, 1997.

C.F. Gottlieb, et al. "Interstitial Microwave Hyperthermia Applicators having Submillimetre Diameters", Int. J. Hyperthermia, vol. 6, No. 3, pp. 707-714, 1990.

Sylvain Labonte, et al., "Monopole Antennas for Microwave Catheter Ablation", IEEE Trans. on Microwave Theory and Techniques, vol. 44, No. 10, pp. 1832-1840, Oct. 1995.

Magdy F. Iskander, et al., "Design Optimization of Interstitial Antennas", IEEE Transactions on Biomedical Engineering, vol. 36, No. 2, Feb. 1989, pp. 238-246.

C.H. Durney, et al., "Antennas for Medical Applications", Antenna Handbook: Theory Application and Design, p. 24-40, Van Nostrand Reinhold, 1988 New York, V.T. Lo, S.W. Lee.

Murakami, R. et al., (1995). "Treatment of Hepatocellular Carcinoma: Value of Percutaneous Microwave Coagulation," American Journal of Radiology (AJR) 164:1159-1164.

Seki, T. et al., (1994). "Ultrasonically Guided Percutaneous Microwave Coagulation Therapy for Small Hepatocellular Carcinoma," Cancer 74(3): 817-825.

European Search Report from Application EP 05021935 dated Jan. 27, 2006.

European Search Report from Application EP 05021939 dated Jan. 27, 2006.

European Search Report from Application EP 05021025 dated Mar. 13, 2006.

European Search Report from Application EP 05021936.9 dated Feb. 6, 2006.

European Search Report from Application EP 05025423.4 dated Jan. 12, 2007.

European Search Report from Application EP 06019768 dated Jan. 8, 2007.

European Search Report from Application EP 05025424 dated Jan. 23, 2007.

European Search Report from Application EP 07009028 dated Jul. 16, 2007.

European Search Report from Application EP 08004975 dated Jul. 24, 2008.

International Search Report for patent application No. EP 03 72 1482 dated Feb. 6, 2006.

International Search Report for International Application No. PCT/US03/09483 dated Aug. 13, 2003.

International Search Report for International Application No. EP 07 01 8821 dated Jan. 14, 2008.

\* cited by examiner

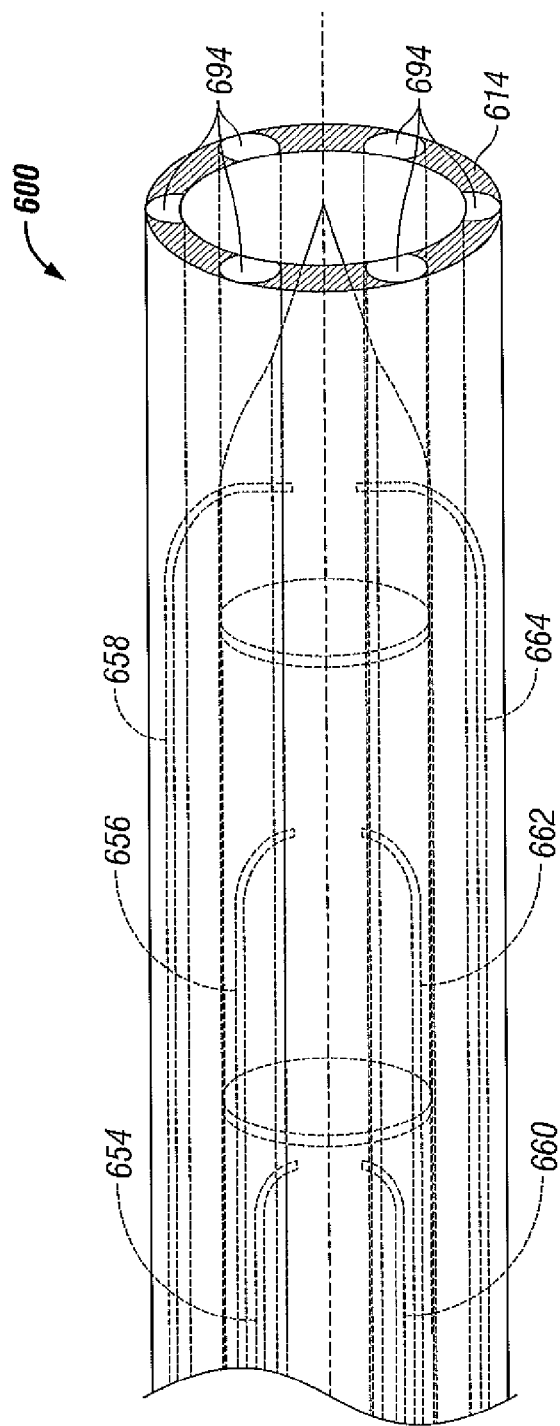
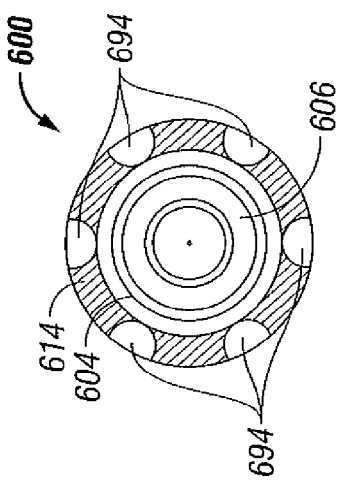
FIG. 8C
FIG. 8D

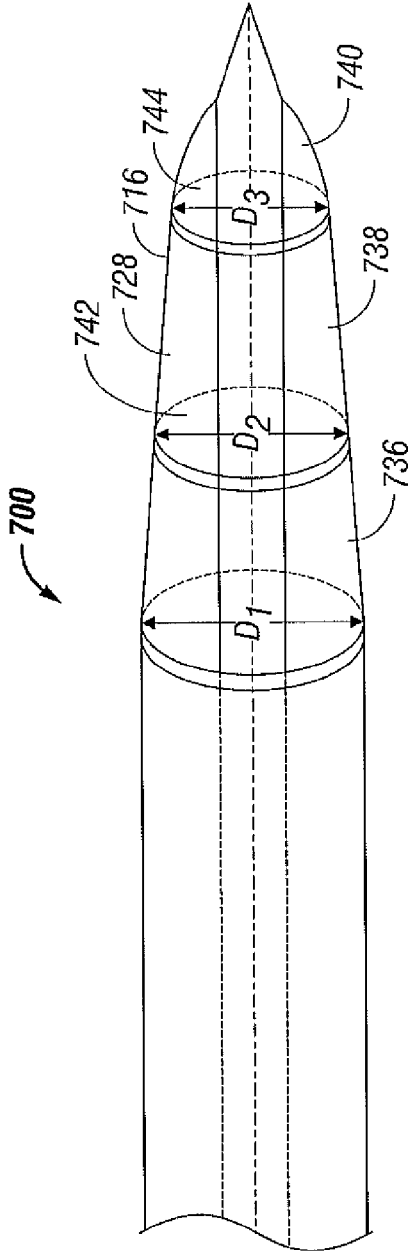
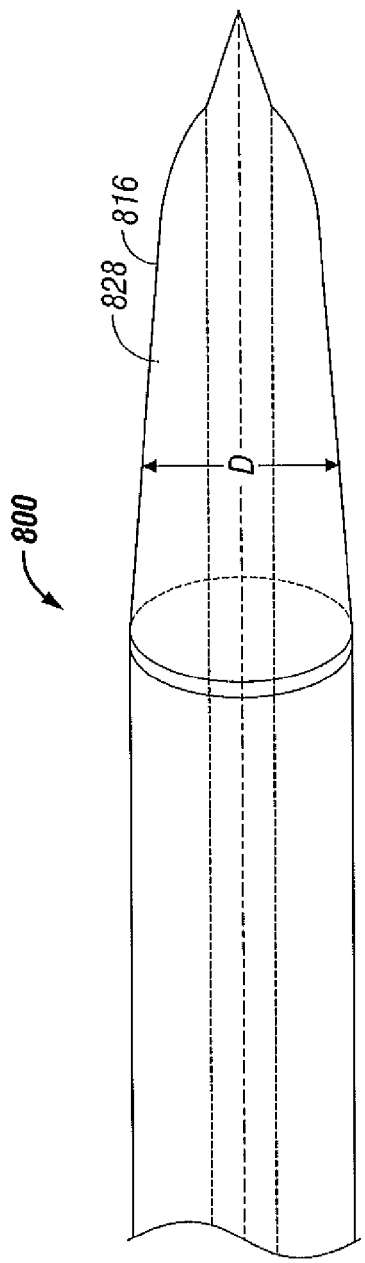
FIG. 9
FIG. 10

TARGETED COOLING OF DEPLOYABLE MICROWAVE ANTENNA

CROSS-REFERENCE TO RELATED APPLICATIONS

The present application claims the benefit of, and priority to, U.S. Provisional Patent Application 60/990,350, filed Nov. 27, 2007, the entire contents of which are hereby incorporated by reference.

BACKGROUND

1. Technical Field

The invention relates generally to microwave antennas that may be used in therapeutic or ablative tissue treatment applications. More particularly, the invention relates to devices and methods for regulating, maintaining, and/or controlling a temperature of microwave antennas used in such applications.

2. Background of the Related Art

Many procedures and devices employing microwave technology are well known for their applicability in the treatment, coagulation, and targeted ablation of tissue. During such procedures, the antenna of a microwave probe of the monopole, dipole, or helical variety, as is conventional in the art, is typically advanced into the patient either laparoscopically or percutaneously until the target tissue is reached.

Following the introduction of the microwave probe, during the transmission of microwave energy to the target tissue, the outer surface of the antenna may sometimes reach unnecessarily high temperatures due to ohmic heating. When exposed to such temperatures, the treatment site, as well as the surrounding tissue, may be unnecessarily and unintentionally effected. The present disclosure contemplates curtailing such tissue effects by providing improved microwave tissue treatment devices, cooling systems, and methods.

To prevent such unnecessarily high temperatures, several different cooling methodologies are conventionally employed.

SUMMARY

A need exists in the art for an improved microwave tissue treatment device incorporating a cooling or temperature control system that minimizes unnecessarily high temperatures during tissue treatment.

The present disclosure is directed to a microwave tissue treatment device for the therapeutic treatment or ablation of tissue. In one embodiment, a microwave tissue treatment device is disclosed that includes an antenna assembly having an elongate member with proximal and distal ends that defines a longitudinal axis, outer and inner conductors disposed within the elongate member that extend along the longitudinal axis, a dielectric material interposed between the outer and inner conductors, and a sleeve at least partially disposed about a distal portion of the inner conductor and defining a cavity therearound, the cavity having a proximal end and a distal end. At least a portion of the inner conductor is deployable such that the antenna assembly may transition from a first position to a second position. The device also includes a cooling system associated with the antenna assembly that includes at least one inflow member and at least one outflow member, each of which is configured to circulate at least one fluid within the cavity such that at least a section of the inner conductor is in fluid contact therewith.

The cavity defined by the sleeve may include at least two regions, such as, for example, a proximal region, an intermediate region, and a distal region. In one embodiment, the microwave tissue treatment device includes at least one baffle member for defining at least two regions of the cavity. In another embodiment, the at least one baffle member defines at least two axial dimensions within the cavity.

In yet another embodiment, the microwave tissue treatment device cooling system includes first, second, and third inflow and outflow members, the first inflow and outflow members, the second inflow and outflow members, and the third inflow and outflow members being in fluid communication with a respective proximal, intermediate, and distal regions of the cavity defined by the sleeve.

The microwave tissue treatment device may include at least one temperature sensor operatively connected to the cavity, or a region thereof.

In another embodiment, the microwave tissue treatment device includes a first baffle member and a second baffle member disposed within the cavity. The first baffle member and the proximal end of the cavity define a proximal region of the cavity of the sleeve, the first baffle member and the second baffle member define an intermediate region of the cavity, and the second baffle member and the distal end of the cavity define a distal region of the cavity. The first baffle member is configured to substantially prevent the communication of fluid between the proximal and intermediate regions, while the second baffle member is configured to substantially prevent the communication of fluid between the intermediate region and the distal region. The first baffle member and the proximal end of the cavity define a first axial dimension, while the first baffle member and the second baffle member define a second axial dimension, and the second baffle member and the distal end of the cavity define a third axial dimension. In one embodiment, the first axial dimension is greater than the second axial dimension.

In another embodiment, the proximal region of the cavity has a first internal diameter, and the intermediate and distal regions have second and third internal diameters, respectively. In one embodiment, the first internal diameter is greater than the second internal diameter, and the second internal diameter is greater than the third internal diameter.

In one embodiment of the present disclosure, at least a portion of the inner conductor has a substantially arcuate profile when deployed, whereas in an alternate embodiment, at least a portion of the inner conductor has a substantially non-arcuate profile when deployed. In another embodiment, at least a portion of the inner conductor has a substantially tapered profile.

The fluid may be chosen from the group consisting of water, saline, ammonium chloride, sodium nitrate, and potassium chloride, and the fluid may be circulated with a pump.

According to another aspect of the present disclosure, an improved microwave tissue treatment device is disclosed that includes an antenna assembly having an outer conductor and an inner conductor with a dielectric material interposed therebetween, where at least a portion of the inner conductor is deployable. The device also includes a sleeve that is at least partially disposed about a distal portion of the inner conductor, thereby defining at least one cavity, at least one baffle member disposed within the sleeve such that at least two regions of the cavity is defined, and a cooling system. The cooling system includes at least one inflow member and at least one outflow member, each of which is in fluid communication with the cavity defined by the sleeve.

According to a further aspect of the present disclosure, a method of cooling a microwave antenna includes providing a cooling system including at least one inflow and outflow member, each being in fluid communication with at least a portion of the microwave antenna, and flowing a cooling fluid through the cooling system such that the cooling fluid is in fluid communication with at least a portion of the microwave antenna.

These and other features of the microwave tissue treatment device and method of use disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein:

FIG. 8C is a perspective view of an antenna assembly of a microwave tissue treatment device, including a cooling system, according to yet another embodiment of the present disclosure;

FIG. 8D is a front view of the antenna assembly of FIG. 8C;

FIG. 9 is a side, plan view of an antenna assembly of a microwave tissue treatment device in accordance with another embodiment of the present disclosure;

FIG. 10 is a side, plan view of an antenna assembly of a microwave tissue treatment device in accordance with yet another embodiment of the present disclosure;

DETAILED DESCRIPTION OF THE EMBODIMENTS

Figure 1:
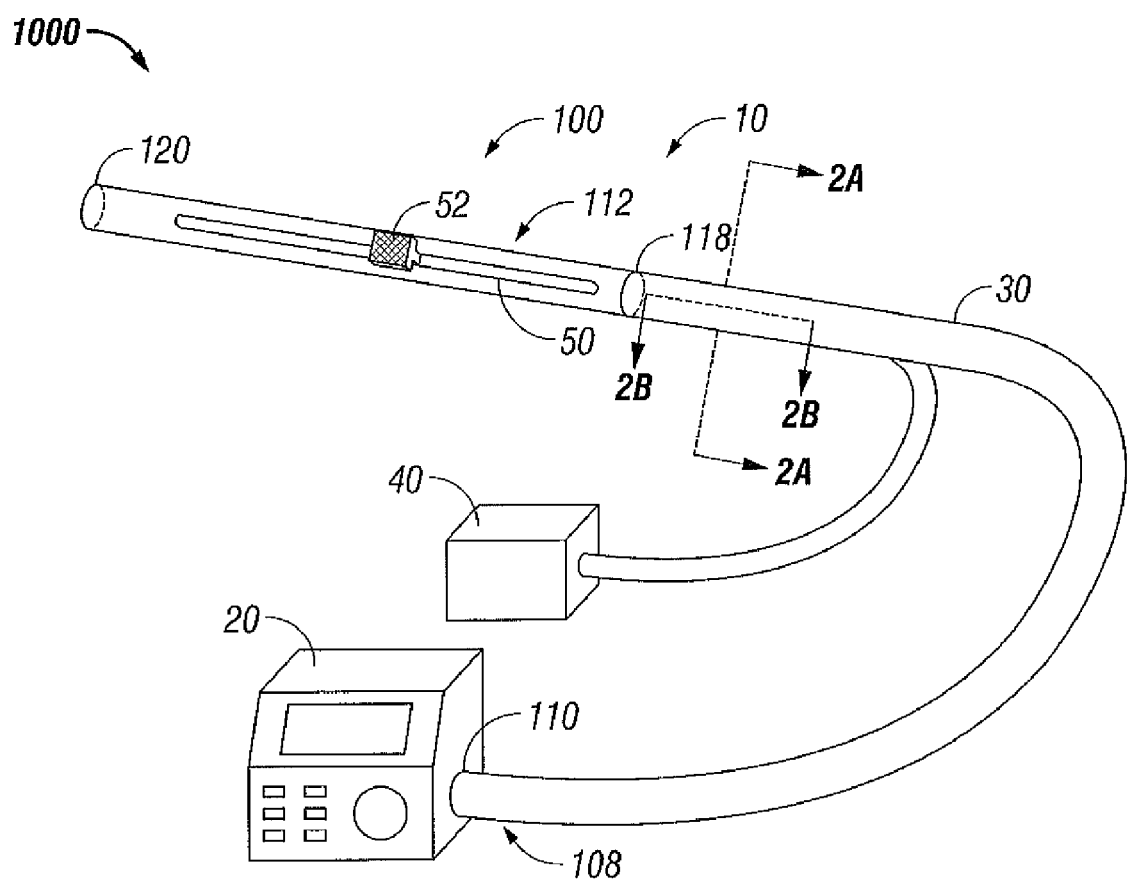
FIG. 1 is a schematic illustration of a microwave tissue treatment system including a microwave tissue treatment device, in accordance with an embodiment of the present disclosure.

In the drawings and in the description that follows, the term "proximal", as is traditional, will refer to the end of the apparatus that is closest to the clinician, while the term "distal" will refer to the end that is furthest from the clinician.

Referring now in detail to the figures, in which like references numerals identify similar or identical elements, there is illustrated, in FIG. 1, a microwave tissue treatment system 10 in accordance with the present disclosure. System 10 includes a microwave tissue treatment device 1000 having an antenna assembly 100 connected to a power source or supply 20, e.g. a microwave or RF generator or any suitable power generating device suitable for energizing the tissue treatment device 1000, through a feedline 30. Microwave tissue treatment device 1000 may include a pump 40, e.g. a peristaltic pump or the like, as a mechanism for circulating a cooling or heat dissipative fluid through device 1000, as described below. Device 1000 may further include a pusher or deployment assembly 50 that includes a deployment knob 52, where deployment knob 52 is operatively engaged with or coupled to the antenna assembly 100, as described in further detail below.

Figure 2A:
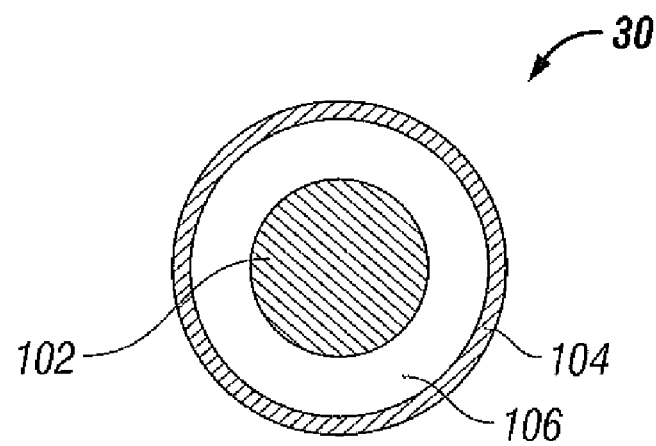
FIG. 2A is a transverse, cross-sectional view of a feedline of the microwave tissue treatment device of FIG. 1, as taken through 2A-2A of FIG. 1.
Figure 2B:
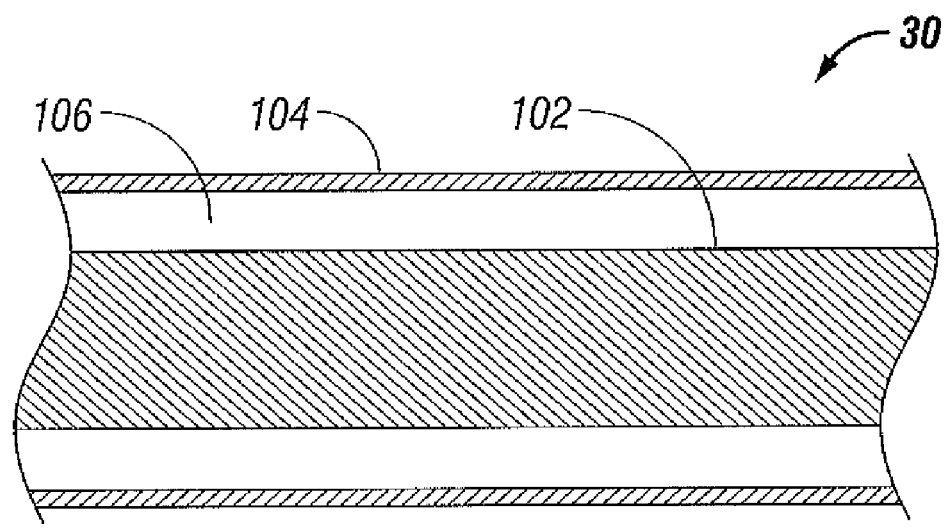
FIG. 2B is a longitudinal, cross-sectional view of the feedline of the microwave tissue treatment device of FIG. 1, as taken through 2B-2B of FIG. 1.

Referring now to FIGS. 1-2B, as indicated above, device 1000 is electrically connected to generator or power supply 20 by feedline 30. Feedline 30 may be any suitable conductive pathway capable of transferring an electrical current to tissue treatment device 1000. In one embodiment, as seen in FIGS. 2A-2B, feedline 30 may be a coaxial cable composed of an inner conductor 102, an outer conductor 104, and a dielectric 106 interposed between inner and outer conductors 102, 104 to electrically separate and/or isolate inner and outer conductors 102,104 from one another. Inner and outer conductors 102, 104 may each be made of a suitable conductive material that may be semi-rigid or flexible, while dielectric 106 may include any number of suitable non-conductive materials such as ceramic and polytetrafluoroethylene (PTFE). Inner and outer conductors 102, 104 of feedline 30 may incorporate any suitable conductive material or metal, including, but not limited to, silver, copper and gold. In certain embodiments, inner and outer conductors 102, 104 of feedline 30 may include a conductive or non-conductive substrate plated or coated with a suitable conductive material.

Feedline 30 may range in length from about 1 foot (0.3048 m) to about 15 feet (4.572 m), or greater, if required in a particular application. As depicted in FIG. 1, feedline 30 has a proximal portion 108 operatively connected to, or connectable to, power supply 20 at proximal end 110, and a distal portion 112 that forms a part of microwave tissue treatment device 1000, as disclosed below.

Figure 3:
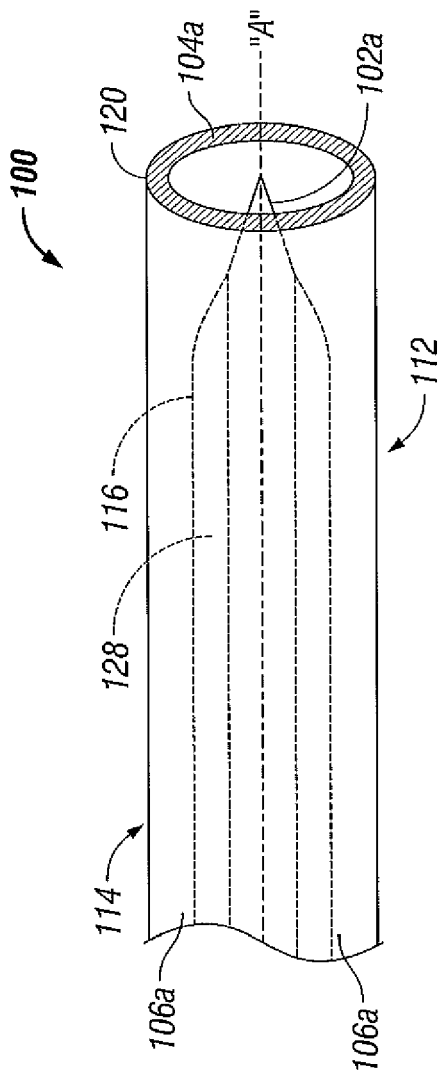
FIG. 3 is a perspective view of an antenna assembly of a microwave tissue treatment device, in accordance with an embodiment of the present disclosure, shown in a non-deployed condition.
Figure 4:
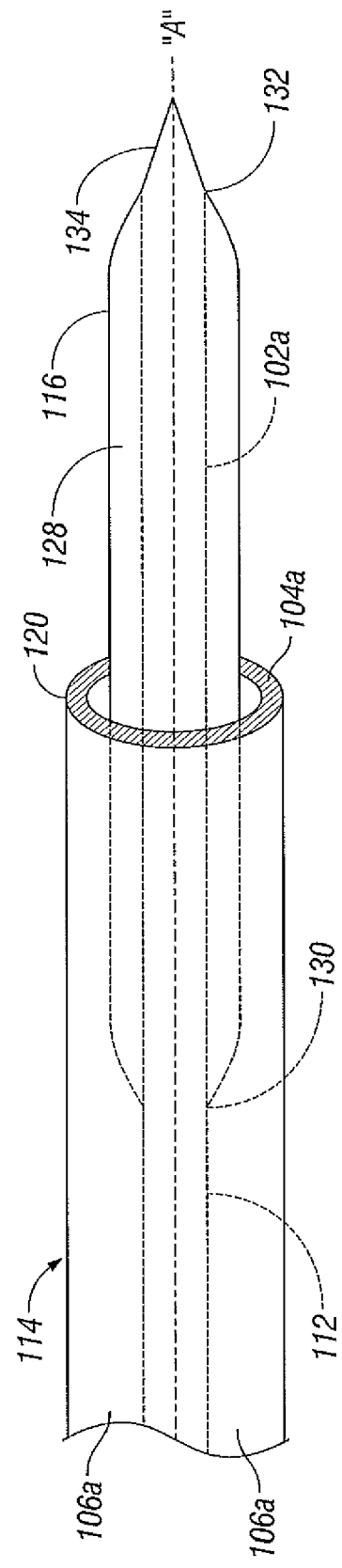
FIG. 4 is a perspective view of the antenna assembly of FIG. 3, shown in a deployed, linear condition.

Referring now to FIGS. 1, 3 and 4, microwave tissue treatment device 1000 includes an antenna assembly 100 having an elongate member 114 disposed about a distal portion 112 of feedline 30, and a sleeve 116 that at least partially surrounds a distal portion 102a of the inner conductor, as described in further detail below.

Elongate member 114 has proximal and distal ends 118, 120 and defines longitudinal axis "A". Elongate member 114 may be formed of any material suitable for electrically insulating a clinician or operator from the inner and outer conductors 102, 104 of feedline 30 disposed therein such that the antenna assembly 100 may be handled during use.

Elongate member 114 conceals a distal portion 102a (FIG. 3) of the inner conductor 102 when the microwave tissue treatment device 1000 is not in use so as to prevent unintentional damage or injury, as well as the distal portion 112 of feedline 30, which includes distal portions 102a, 104a, and 106a of the inner conductor, the outer conductor, and the dielectric, respectively. Accordingly, the inner conductor, the outer conductor, and the dielectric are not only components of the feedline 30, but also constitute components of antenna assembly 100.

At least a portion of the inner conductor, i.e. distal portion 102a, is deployable from distal portion 104a of the outer conductor, such that the antenna assembly 100 may transition from a first, non-deployed condition (FIG. 3), to a second, deployed condition during use (FIG. 4), as described in further detail below. In the first condition, the distal portion 102a of the inner conductor is at least partially disposed within the distal portion 104a of the outer conductor and the elongate member 114. In the second, deployed condition, the distal portion 102a of the inner conductor extends at least partially beyond a distal end 120 of elongate member 114, such that contact may be made with the target tissue (not shown).

Movement from the first position to the second position may be facilitated through the use of any suitable mechanism, such as, for example, a deployment assembly 50 (FIG. 1). Reference may be made to commonly owned U.S. Patent Publication No. 2004/0267156, filed Apr. 4, 2004, for a detailed discussion regarding the components and functionality of deployment assembly 50.

Figure 5:
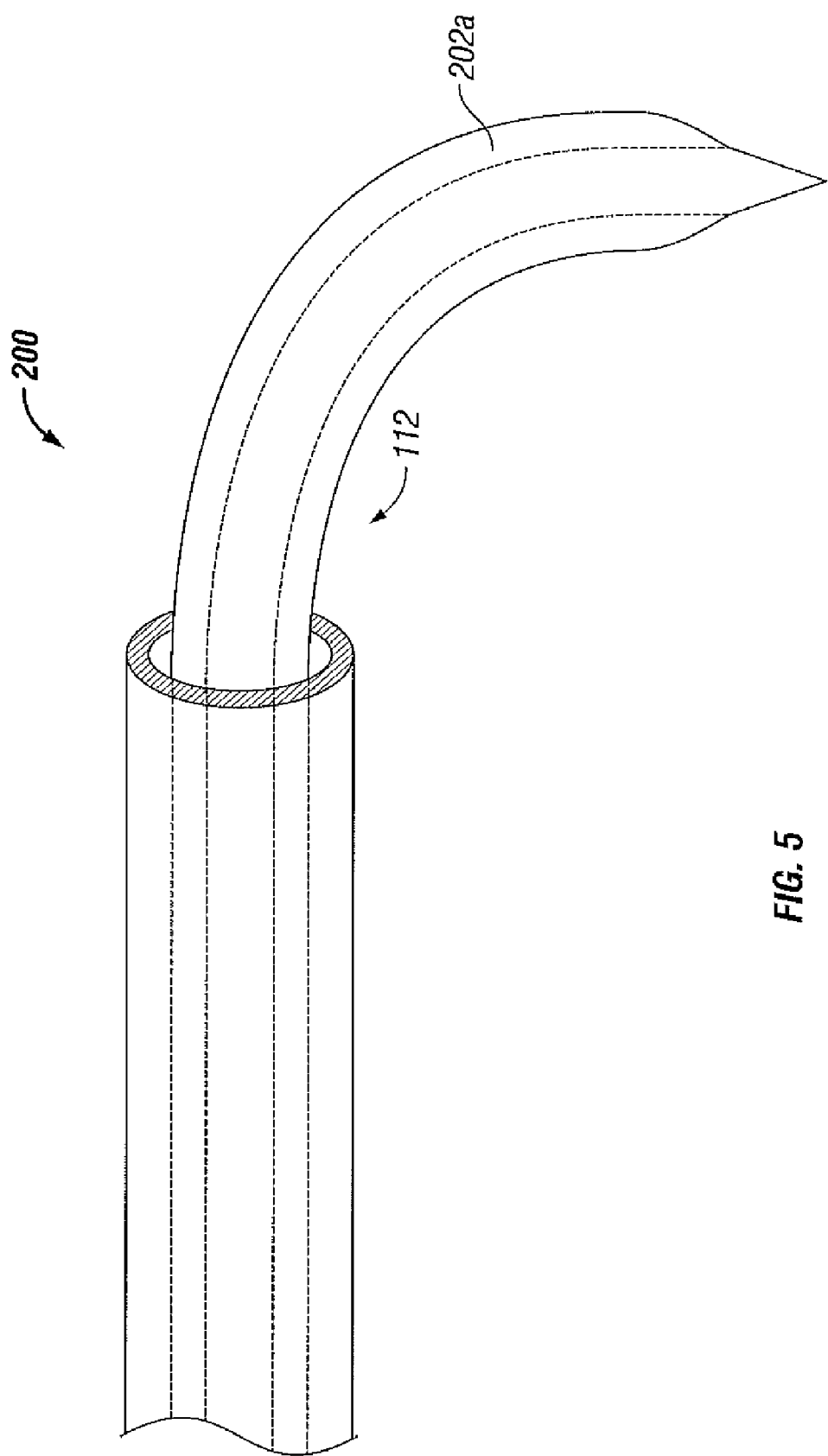
FIG. 5 is a perspective view of an antenna assembly of a microwave tissue treatment device, in accordance with an embodiment of the present disclosure, shown in a deployed, arcuate condition.

In one embodiment, as seen in FIG. 4, antenna assembly 100 includes a distal portion 102a of an inner conductor that exhibits a substantially non-arcuate profile when deployed. In an alternate embodiment, as seen in FIG. 5, antenna assembly 200 includes an inner conductor with a distal portion 202a that exhibits a substantially arcuate profile when deployed. Reference may be made to commonly owned U.S. Pat. No. 7,197,363 for a detailed discussion of the structure of arcuate microwave antenna configurations.

Figure 6:
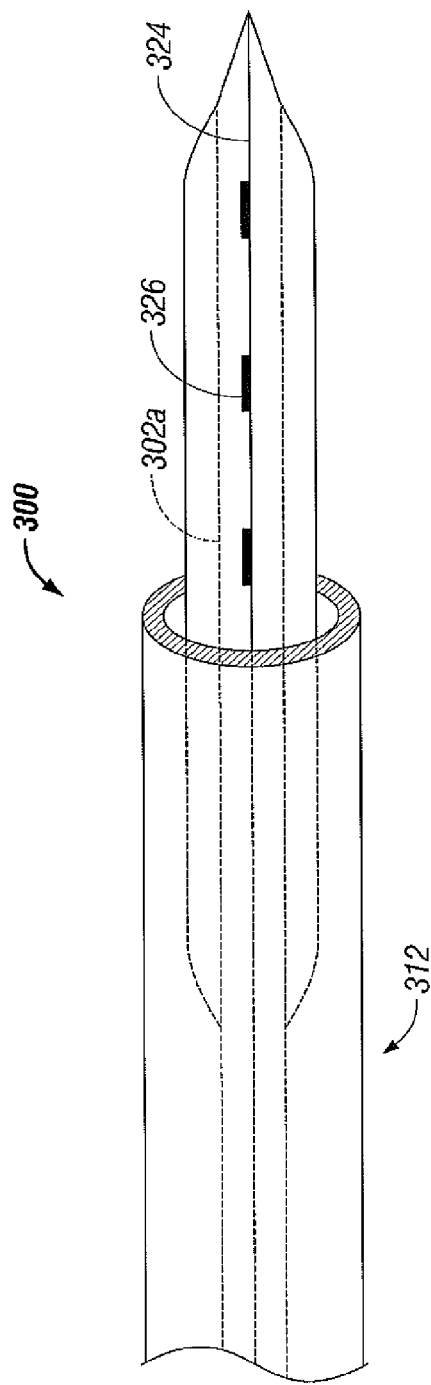
FIG. 6 is a perspective view of an antenna assembly of a microwave tissue treatment device, in accordance with another embodiment of the present disclosure, shown in a deployed condition.

In another embodiment, as seen in FIG. 6, antenna assembly 300 includes a distal portion 302a of an inner conductor that is not entirely formed of a conductive material. In this embodiment, distal portion 302a of the inner conductor includes a radiating member 324 with one or more conductive surfaces 326. Conductive surface or surfaces 326 may have a particular pattern or distribution for focusing or dispersing the energy transmitted into distal portion 302a of the inner conductor. For example, radiating member 324 may have a conductive surface 326 on only one side or in one particular area or region thereof.

Figure 7:
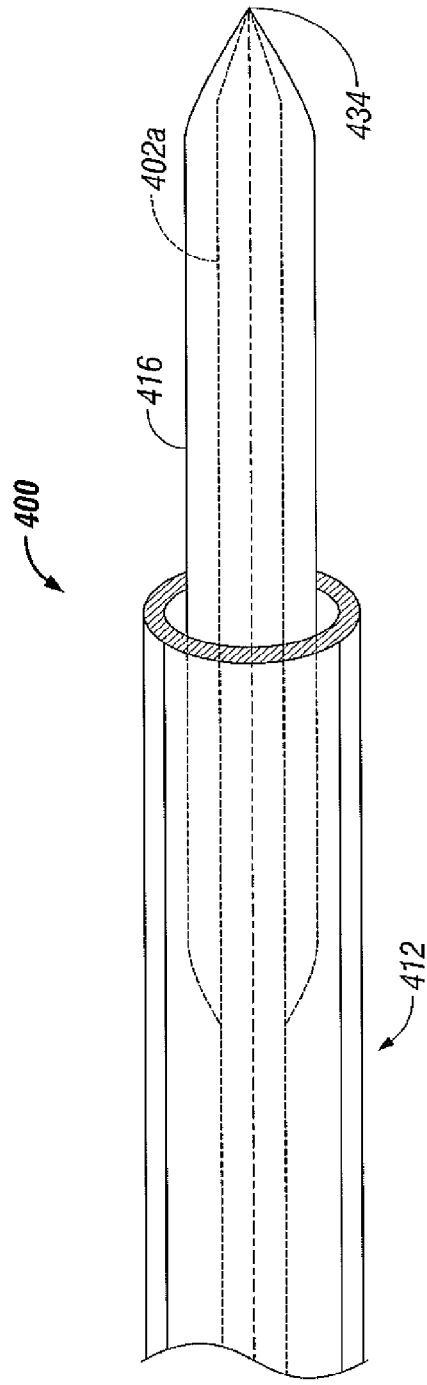
FIG. 7 is a perspective view of an antenna assembly of a microwave tissue treatment device in accordance with another embodiment of the present disclosure, shown in a deployed condition.

Referring back to FIGS. 3 and 4, sleeve 116 is disposed about distal portion 102a of the inner conductor in such a manner so as to define a cavity 128. Sleeve 116 may be fixedly, releasably, or slidably connected to distal portion 102a in any suitable manner including, but not being limited to, welding or adhering, as would be appreciated by one skilled in the art. Sleeve 116 has proximal and distal ends 130, 132 defined by the points at which sleeve 116 is connected to distal portion 102a. In one embodiment, as best seen in FIG. 4, the distal-most tip 134 of distal portion 102a extends beyond the distal end 132 of sleeve 116. In another embodiment, however, as best seen in FIG. 7, antenna assembly 400 may include a sleeve 416 connected to a distal portion 402a of an inner conductor at the distal-most tip 434 thereof, or at a point therebeyond (not shown).

Referring again to FIGS. 3 and 4, proximal end 130 of sleeve 116 may be located at any suitable location along the length of distal portion 102a of the inner conductor, dependent upon the desired volume of cavity 128. Although depicted as substantially incisive, the present disclosure contemplates that distal-most tip 134 may be substantially arcuate, duckbilled, or any other such configuration suitable for facilitating the entry of the microwave tissue treatment device into the tissue of a patient.

Sleeve 116 may be formed of any suitable biocompatible, impermeable material capable of retaining fluid therein, including and not limited to PTFE and tetrafluoroethylene-perfluorpropylene (FEP). The present disclosure contemplates that sleeve 116 may be either substantially rigid, or substantially non-rigid in character.

Figure 8:
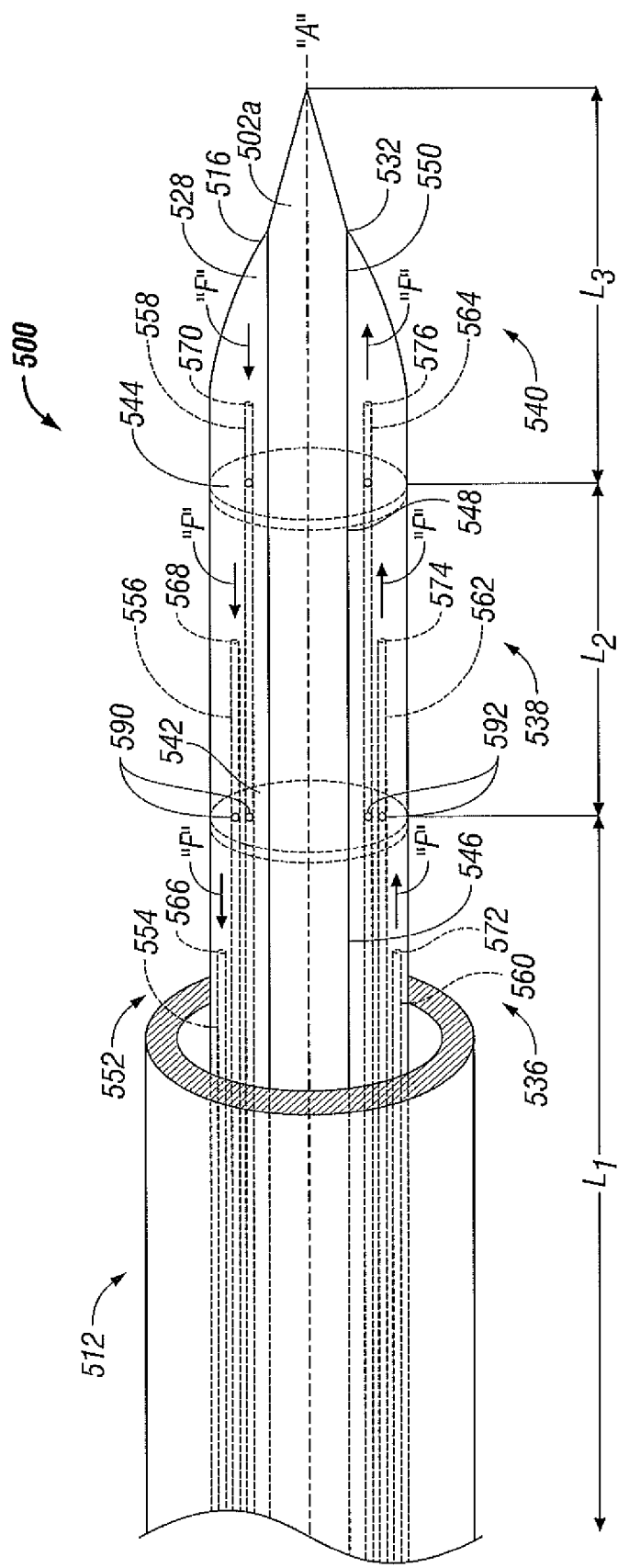
FIG. 8 is a perspective view of an antenna assembly of a microwave tissue treatment, including a cooling system, according to one embodiment of the present disclosure.
Figure 8A:
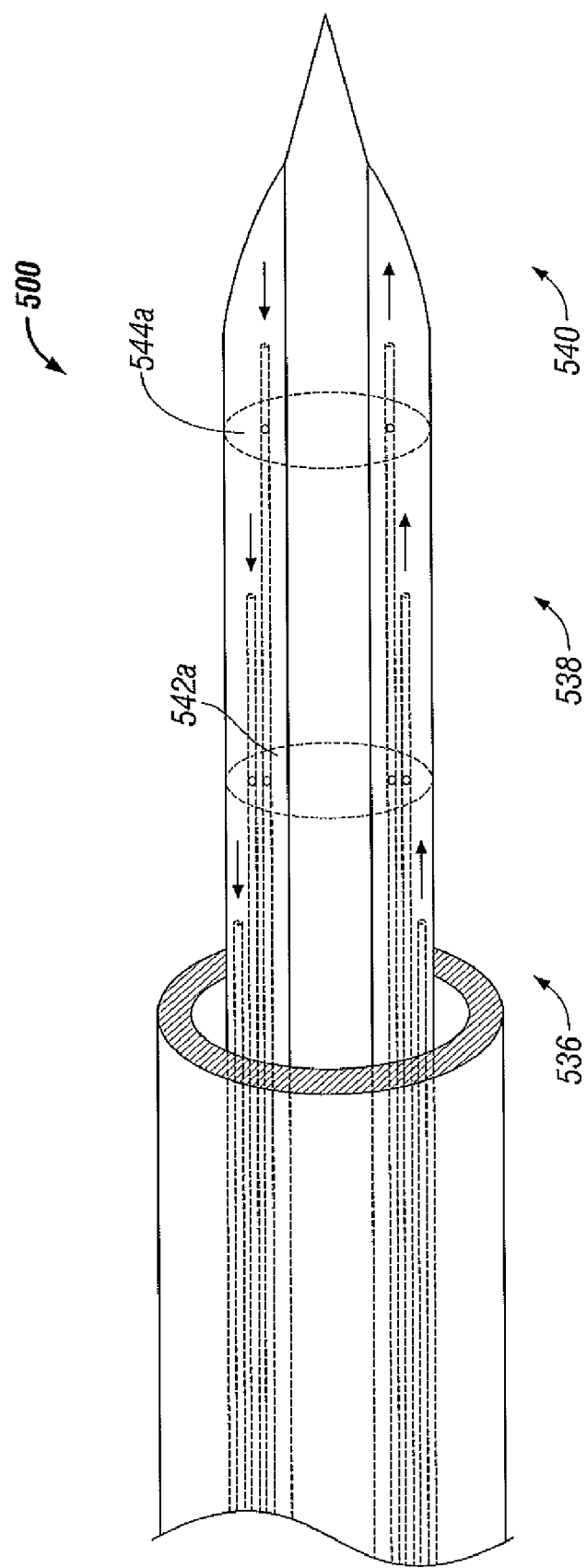
FIG. 8A is a perspective view of an antenna assembly of a microwave tissue treatment, including a cooling system, according to another embodiment of the present disclosure.

In one embodiment, as seen in FIG. 8, antenna assembly 500 includes a sleeve 516 defining a cavity 528 around a distal portion 502a of an inner conductor, and one or more baffle member(s) 542, 544 disposed within sleeve 516 that function to divide or compartmentalize cavity 528 into individual regions 536, 538, 540. Each region 536, 538, 540 defines a respective section 546, 548, 550 of the distal portion 502a of the inner conductor. In an alternate embodiment, as seen in FIG. 8A, the individual regions 536, 538, 540 are not defined by physical baffle members 542, 544 (FIG. 8), but are rather defined constructively as virtual baffle members $542_A$, $544_A$ by the interaction of a corresponding number of fluids, e.g. one fluid within each of individual regions 536, 583, 540, which may be immiscible. The incorporation of one or more fluids into antenna assembly 500 will be discussed in further detail below.

First or proximal region 536 and first section 546 of distal portion 502a have a first axial dimension $L_1$, and are defined by the location of the proximal end (not shown) of the sleeve 516 and the location of first baffle member 542. Second or intermediate region 538 and second section 548 of distal portion 502a have a second axial dimension $L_2$, and are defined by the location of first baffle member 542 and the location of second baffle member 544. And third or distal region 540 and third section 550 of distal portion 502a have a corresponding third axial dimension $L_3$, and are defined by the location of second baffle member 544 and the location of distal end 532 of sleeve 516.

In this embodiment, first and second baffle members 542, 544, respectively, serve not only to define the metes of the three regions 536, 538, 540 of cavity 528 of sleeve 516, in conjunction with the proximal end 528 (not shown) and the distal end 530 thereof, but also serve to substantially prevent any co-mingling of cooling fluid or fluids that may be circulated throughout each of the proximal, intermediate, and distal regions 536, 538, 540, as described below. The present disclosure contemplates that cavity 528 of sleeve 516 may be divided into any suitable number of regions dependent upon the requirements of the procedure and the application in which the microwave tissue treatment device may be employed.

With continued reference to FIG. 8, third or distal section 550 of the distal portion 502a of the inner conductor may comprise the area of active heating during tissue treatment or ablation. It may be desirable, therefore, to prevent the temperature in distal section 550 from reaching excessively high temperatures in order to maintain optimal energy delivery and to maintain optimal thermal therapy of the tissue. Second or intermediate section 548 of distal portion 502a may also become hot due to ohmic and conductive heating from distal section 550. Since intermediate section 548 may be in contact with the tissue surrounding the target site, it may be desirable to allow intermediate section 548 to achieve a particular temperature profile dependent upon the procedure in which the antenna assembly 500 is employed.

As an illustrative example, where coagulation of the insertion tract may be desirable, the clinician may want to allow intermediate section 548 of distal portion 502a of the inner conductor to attain a particular predetermined temperature capable of creating a coagulating effect in the insertion tract. In other applications, it may also be desirable, however, to prevent the temperature in intermediate section 548 from rising beyond a particular threshold to protect surrounding sensitive tissue structures from undesired effects. During use, first or proximal section 546 of distal portion 502a may also come into contact with the skin of a patient. Accordingly, since proximal section 546 of distal portion 502a may also be subject to ohmic and/or conductive heating, it may therefore be desirable to maintain the temperature of this section below a specific temperature, particularly in percutaneous or laparoscopic procedures, to prevent undesired effects upon the skin surface of the patient. In other procedures, such as in applications where lesions are located deep within the tissue, it may be desirable to allow the proximal section 546 to become heated to allow for the coagulation of the insertion tract.

With continued reference to FIG. 8, antenna assembly 500 further includes a cooling system 552 for regulating the temperature of distal portion 502a of the inner conductor. The cooling system 552 operates in conjunction with, and is fluidly connected to, cavity 528 of sleeve 516 such that one or more cooling or heat dissipative fluids "F" may be circulated therethrough. Fluid "F" serves to dissipate some of the heat generated by the antenna assembly 500 during use and may also act as a medium that modifies the dielectric constant of the distal portion of the antenna assembly. Potential dissipative fluids include, but are not limited to, water, saline, liquid chlorodifluoromethane, or any suitable perfluorocarbon fluid, such as Fluorinert®, distributed commercially by Minnesota Mining and Manufacturing Company (3M™), St. Paul, Minn., USA. The fluid circulated through cooling system 552 may vary depending upon the desired cooling rate and the desired tissue impedance matching properties. In various embodiments, gases, such as air, nitrous oxide, nitrogen, carbon dioxide, etc., may also be utilized as the dissipative fluid. In yet another variation, a combination of liquids and/or gases may be utilized.

During circulation, the heat dissipative fluid is in contact with those sections 546, 548, 550 of distal portion 502a of the inner conductor within respective regions 536, 538, 540 of cavity 528 defined by sleeve 516 such that the heat generated therein may be dissipated through the fluid "F". The cooling system 552 includes one or more inflow tubes 554, 556, 558, and one or more respective outflow tubes 560, 562, 564 to circulate the dissipative fluid "F". Cooling system 552 may also include at least one pump 40 (FIG. 1) in fluid communication with each inflow tube 554, 556, 558 and each outflow tube 560, 562, 564 for facilitating the circulation of the dissipative fluid "F".

Cooling system 552 may include any number of inflow and outflow tubes suitable for circulating a dissipative fluid throughout the cavity 528 defined by sleeve 516, and/or any individual regions thereof. Cooling system 552 may also employ any number of inflow and outflow members in fluid communication with each section 546, 548, 550 of distal portion 502a of the inner conductor. In some embodiments, one or more regions of cavity 528 may not be in fluid communication with cooling system 552.

As seen in FIG. 8, each of the proximal, intermediate, and distal regions 536, 538, 540, respectively, has a corresponding inflow tube 554, 556, and 558 in fluid communication therewith, and a corresponding outflow tube 560, 562, and 564 in fluid communication therewith. In particular, a proximal end (not shown) of first inflow tube 554 may be connected to pump 40 (FIG. 1), while a distal end 566 of first inflow tube 554 is in fluid communication with proximal region 536, thereby allowing dissipative fluid to flow, either constantly or intermittently, into the proximal region 536 of cavity 528 defined by sleeve 516. Upon entering proximal region 536, the dissipative fluid "F" comes into direct contact with the proximal section 546 of distal portion 502a of the inner conductor, allowing for the direct convective cooling of proximal section 546. In conjunction with first inflow tube 554, a proximal end (not shown) of first outflow tube 560 may be connected to pump 40 (FIG. 1), while a distal end 572 of first outflow tube is in fluid communication with proximal region 536, thereby allowing the dissipative fluid "F" to flow, either constantly or intermittently, out of the proximal region 536, and return to the pump 40 (FIG. 1). In so doing, during operation, heat generated by proximal section 546 of distal portion 502a of the inner conductor, disposed within the proximal region 536 of the cavity 528 defined by sleeve 516, may be regulated and/or dissipated.

As with the proximal region 536, a dissipative fluid may be pumped into and out of intermediate region 538 through respective distal ends 568, 574 of the second inflow and outflow tubes 556, 562 thereby dissipating the heat generated by the intermediate section 548 of distal portion 502a of the inner conductor through the fluid circulated therein.

Likewise, a dissipative fluid may also be circulated into and out of the distal region 540 through respective distal ends 570, 576 of the third inflow and outflow tubes 558, 564 thereby dissipating the heat generated by the distal section 550 of distal portion 502a of the inner conductor through the fluid circulated therein. In some embodiments, the fluid may act as a medium that modifies the dielectric constant of the antenna.

With continuing reference to FIG. 8, inflow tubes 554, 556, 558 may enter cavity 528 through apertures (not shown) at the proximal end of sleeve 516 (not shown). First inflow tube 554 and first outflow tube 560 are configured such that their respective distal ends 568, 580 are in fluid communication with proximal region 536. Second and third inflow tubes 556, 558 and second and third outflow tubes 562, 564 may continue through proximal region 536, through apertures 590 in first baffle member 542, and into intermediate region 538. Second inflow tube 556 and second outflow tube 562 are configured such that their respective distal ends 572, 584 are in fluid communication with intermediate region 538. Third inflow and outflow tubes 558, 564 continue through intermediate region 538, through apertures 590 in second baffle member 544, and into distal region 540. Third inflow and outflow tubes 558, 564 are configured such that their respective distal ends 576, 588 are in fluid communication with distal region 540.

In this embodiment, each of the proximal end of the cavity 528, the first baffle member 542, and the second baffle member 544 include seal members 592 associated with apertures 590. Seal members 592 may be any member suitable to substantially prevent the escape of any fluid contained within respective regions of cavity 528, through the apertures 590, including, and not limited to a seal, gasket, or the like. Seal members 592 may be formed of any suitable material, including and not limited to, a polymeric material. Seal members 592 may also substantially prevent the intermingling of the cooling fluids circulated through each of the proximal, intermediate, and distal regions 536, 538, 540 of cavity 528.

Figure 8B:
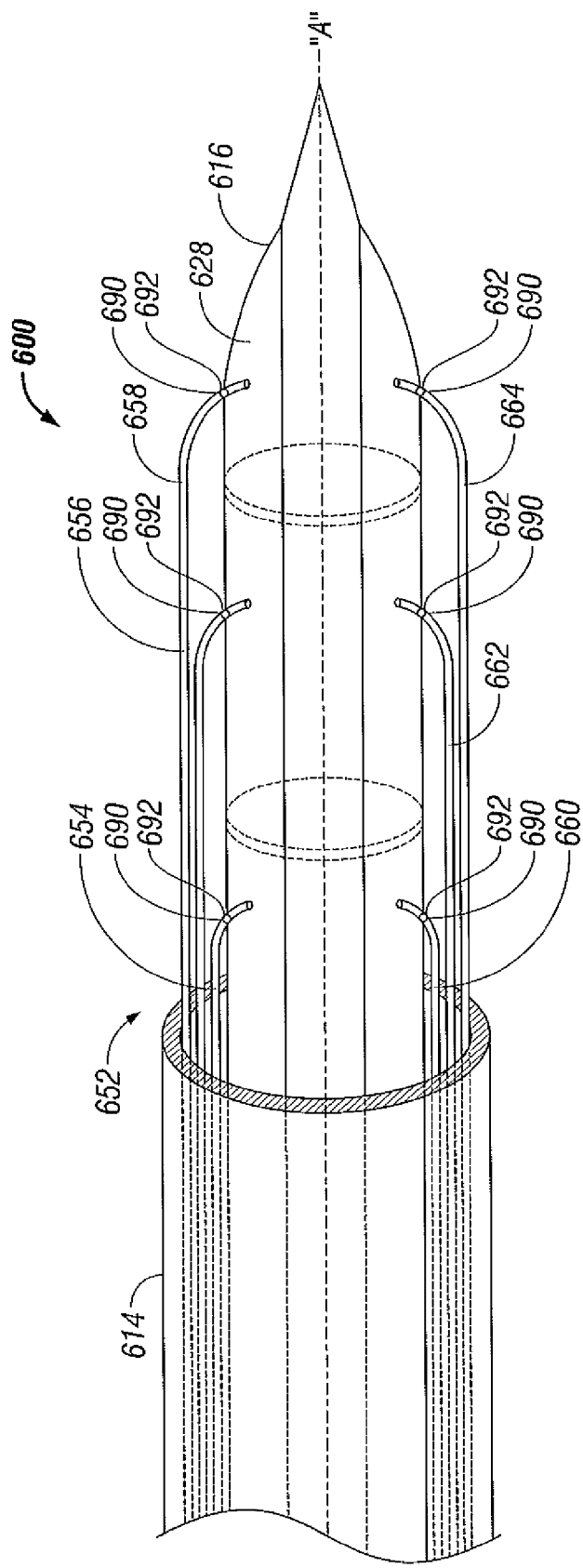
FIG. 8B is a perspective view of an antenna assembly of a microwave tissue treatment device, including a cooling system, according to still another embodiment of the present disclosure.

Referring momentarily to FIG. 8B, antenna assembly 600 includes a cooling system 652 having inflow tubes 654, 656, 658 and outflow tubes 660, 662, 664. In this embodiment, inflow tubes 654, 656, 658 and outflow tubes 660, 662, 664 enter cavity 628 defined by sleeve 616 through apertures 690 formed therein. In this embodiment, inflow tubes 654, 656, 658 may traverse elongate member 614 along its outer surface, connecting to either a common pump 40 (FIG. 1), or to individual pumps, as described above. Correspondingly, outflow tubes 660, 662, 664 may also traverse the outer surface of elongate member 116, connecting to either the common pump 40 (FIG. 1) or to the individual pumps. In this embodiment, sleeve 616 is adapted with sealing member or members 692 at apertures 690 to substantially prevent the escape of any fluid contained in cavity 628 defined by sleeve 616 through apertures 690.

In another embodiment, as seen in FIGS. 8C-8D, antenna assembly 600 may include one or more channels 694 formed in the elongate member 614 that are configured to respectively receive at least a portion of inflow tubes 654, 656, 658 and outflow tubes 660, 662, 664. Alternatively, channels 694 may be formed in outer conductor 604, dielectric material 606, or in any other suitable location.

Referring again to FIG. 8, given the desirability of controlled heating and temperature regulation within the individual sections 546, 548, and 550 of distal portion 502a of the inner conductor and the corresponding regions 536, 538, and 540 of the cavity 528, the axial locations of first and second baffle members 542, 544 within cavity 528 may be varied as desired or necessary. By varying the location of baffle members 542 and 544 in different embodiments, the axial length of the proximal, intermediate and distal regions 536, 538, and 540 may be varied. In varying the axial length of a region, the overall volume of that region may be varied, and accordingly, the volume of dissipative fluid circulated within that region may also be varied. As would be appreciated by one of ordinary skill in the art, an inverse relationship exists between the volume of dissipative fluid within a particular region of the cavity 528 and the temperature of that region, in that as the volume of fluid is increased, the temperature of the region will decrease. As an additional means of regulating temperature, the flow rate of fluid "F" into each regions 536, 538, and 540 of the cavity 528 may be controlled or varied, e.g. through the use of multiple pumps (hot shown).

The baffle members 542, 544 may be located at any suitable or desired point within the cavity 528 defined by the sleeve 516. In one embodiment, baffle members 542, 544 are positioned such that the first, second and third axial dimensions, $L_1$, $L_2$, and $L_3$, respectively, of proximal, intermediate, and distal regions 536, 538, 540 are substantially equivalent. In another embodiment, baffle members 542, 544 are positioned such that the first axial dimension $L_1$, of proximal region 536, is greater than the second and third axial dimensions $L_2$ and $L_3$, respectively, of intermediate and distal regions 538, 540. In yet another embodiment, baffle members 542, 544 are positioned such that the third axial dimension $L_3$, of distal region 540, is greater than the first and second axial dimensions $L_1$ and $L_2$, respectively, of proximal and intermediate regions 536, 538. In alternate embodiments, the present disclosure contemplates locating the baffle members 542, 544 such that the overall volume of the cavity 528 may be distributed amongst any individual regions thereof in any suitable manner.

Figure 12:
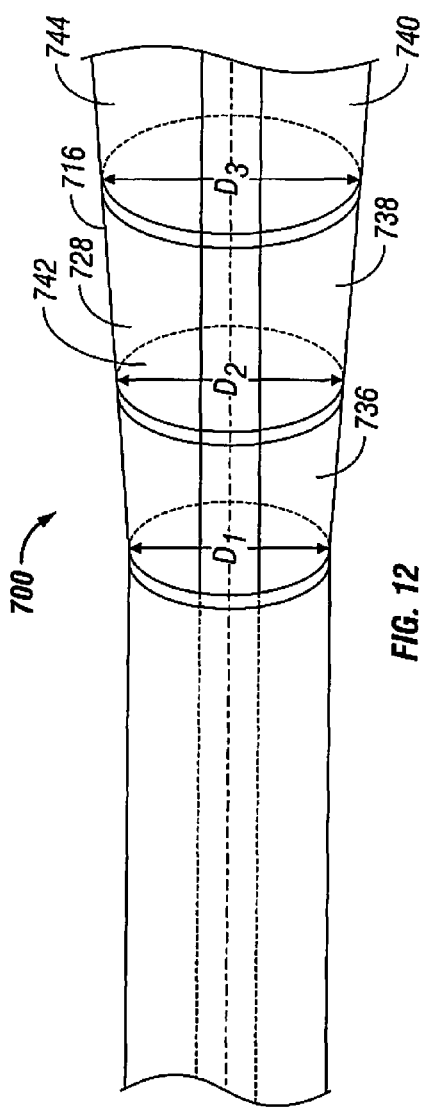
FIG. 12 is a side, plan view of an antenna assembly of a microwave tissue treatment device in accordance with another embodiment of the present disclosure.

Referring now to FIGS. 9 and 12, in other embodiments, antenna assembly 700 includes a sleeve 716 that defines a cavity 728 having proximal, intermediate, and distal regions 736, 738, and 740 defined by first and second baffle members 742, 744. In this embodiment, proximal, intermediate, and distal regions 736, 738, and 740 have a first, a second, and a third radial dimension or diameter $D_1$, $D_2$, and $D_3$, respectively. In accordance with the present disclosure, radial dimensions $D_1$, $D_2$, and $D_3$ of the proximal, intermediate, and distal regions 736, 738, and 740 may be varied so as to control the volume of each region, and accordingly, the volume of dissipative fluid circulated therethrough. By varying the volume of dissipative fluid circulated through each individual region 736, 738, and 740 of the cavity 728, the temperature of each region may be substantially regulated, as discussed above.

In one embodiment, the first, second and third radial dimensions, $D_1$, $D_2$, and $D_3$, respectively, are substantially equivalent. In another embodiment, as illustrated in FIG. 9, the first radial dimension $D_1$, of proximal region 736, is greater than the radial dimensions $D_2$ and $D_3$, respectively, of intermediate and distal regions 738 and 740. In yet another embodiment, as illustrated in FIG. 12, the third radial dimension $D_3$, of distal region 740, is greater than the radial dimensions $D_1$ and $D_2$, respectively, of proximal and intermediate regions 736 and 738. In alternate embodiments, the present disclosure contemplates that the radial dimensions $D_1$, $D_2$, and $D_3$, respectively, of each region 736, 738, and 740 of the cavity 728 defined by the sleeve 716, may be varied in any suitable manner.

Referring now to FIG. 10, in one embodiment, the present disclosure contemplates an antenna assembly 800 that includes a sleeve 816 defining a cavity 828 with a radial dimension D. In this embodiment, radial dimension D of cavity 828 is varied in a continuously decreasing manner over the axial length thereof, such that a generally tapered profile is exhibited. While the antenna assembly 800 includes a sleeve 816 defining a cavity 828 that is not compartmentalized into any regions, the tapered profile may be applicable to any of the embodiments disclosed herein above.

Figure 11:
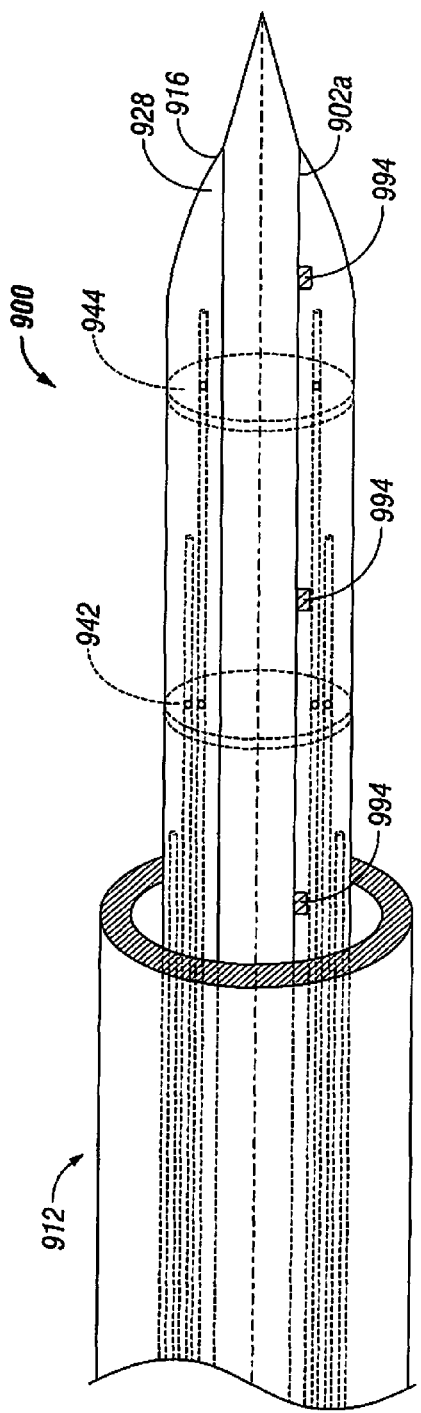
FIG. 11 is a perspective view of an antenna assembly of a microwave tissue treatment device in accordance with another embodiment of the present disclosure, shown in a deployed condition.

In another embodiment, seen in FIG. 11, an antenna assembly 900 is disclosed that includes one or more temperature sensors 994 coupled to a distal portion 902a of an inner conductor for monitoring a temperature fluctuation at or about the distal portion 902a. It may be desirable to monitor the temperature of the distal portion 902a, and/or the tissue that may come into contact therewith, or with sleeve 916, in an effort to guard against overheating and/or the unintended therapeutic effects on the tissue. This may be particularly useful in applications where microwave energy is used for treating or ablating tissue around the radiating portion. In alternate embodiments, temperature sensors 994 may be coupled or otherwise incorporated into antenna assembly 900 at any suitable location, including, but not being limited to sleeve 916, such that the temperature of the distal portion 902a of the inner conductor and/or the cavity 928 may be monitored. In various embodiments, temperature sensor or sensors 994 may be located on the sleeve 916, e.g., on an external surface thereof, or within the sleeve 916, e.g., within the cavity 928 which the sleeve 916 defines, using any suitable means, e.g. adhesives. The temperature sensor or sensors 994 may be located on a baffle member or members 942, 944, if any. Temperature sensors 994 may be configured for electrical connection to power source 20 (FIG. 1).

The temperature sensor or sensors 994 may be a semiconductor-based sensor, a thermister, a thermocouple or other temperature sensor that would be considered as suitable by one skilled in the art. An independent temperature monitor (not shown) may be coupled to the temperature sensor. Alternatively, a power supply with an integrated temperature monitoring circuit (not shown), such as one described in U.S. Pat. No. 5,954,719, may be used to modulate microwave power output supplied to the antenna assembly. Other physiological signals, e.g. EKG, may also be monitored by other medical instrumentation well known to one skilled in the art and such data applied to control the microwave energy delivered to the antenna assembly.

A closed loop control mechanism, such as a feedback controller with a microprocessor, may be implemented for controlling the delivery of energy, e.g., microwave energy, to the target tissue based on temperature measured by the temperature sensor or sensors 994.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A microwave tissue treatment device, comprising:
an antenna assembly including:
an elongate member defining a longitudinal axis and having proximal and distal ends;
an outer conductor and an inner conductor each disposed within the elongate member and extending along the longitudinal axis, wherein at least a portion of the inner conductor is configured to be deployable from the outer conductor such that the antenna assembly may transition from a first position to a second position;
a dielectric material disposed at least in part between the outer conductor and the inner conductor; and
a sleeve at least partially disposed about a distal portion of the inner conductor and defining at least one cavity, the at least one cavity having a proximal end and a distal end, wherein at least a portion of the sleeve is configured to be deployable from within a lumen defined by a distal portion of the outer conductor;
the dielectric material including a distal portion at least partially disposed within the lumen between the sleeve and the distal portion of the outer conductor; and
a cooling system including at least one inflow member and at least one outflow member, the at least one inflow member and the at least one outflow member disposed in fluid communication with the at least one cavity defined by the sleeve, the at least one inflow member and the at least one outflow member configured to circulate at least one fluid within the at least one cavity such that at least a portion of the inner conductor is in fluid contact with the at least one fluid.

2. The microwave tissue treatment device of claim 1, wherein the cavity includes at least two regions.

3. The microwave tissue treatment device of claim 1, wherein the cavity includes a proximal region, an intermediate region, and a distal region.

4. The microwave tissue treatment device of claim 3, wherein the at least one inflow member includes a first inflow member, a second inflow member, and a third inflow member, the at least one outflow member including a first outflow member, a second outflow member, and a third outflow member,
wherein the first inflow member and the first outflow member are in fluid communication with the proximal region, the second inflow member and the second outflow member being in fluid communication with the intermediate region, and the third inflow member and the third outflow member being in fluid communication with the distal region.

5. The microwave tissue treatment device of claim 2, further including at least one baffle member disposed within the cavity, the at least one baffle member defining the at least two regions.

6. The microwave tissue treatment device of claim 5, further including at least one temperature sensor, the at least one temperature sensor operatively connected to at least one of the at least two regions.

7. The microwave tissue treatment device of claim 5, wherein at least a portion of the inner conductor has a substantially tapered profile.

8. The microwave tissue treatment device of claim 4, further including a first baffle member and a second baffle member disposed within the cavity, the first baffle member and the proximal end of the cavity defining the proximal region, the first baffle member and the second baffle member defining the intermediate region, and the second baffle member and the distal end of the cavity defining the distal region, the first baffle member being configured to substantially prevent fluid communication between the proximal region and the intermediate region, the second baffle member being configured to substantially prevent fluid communication between the intermediate region and the distal region, the first baffle member and the proximal end of the cavity defining a first axial dimension therebetween, the first baffle member and the second baffle member defining a second axial dimension therebetween, the second baffle member and the distal end of the cavity defining a third axial dimension.

9. The microwave tissue treatment device of claim 8, wherein the first axial dimension is greater than the second axial dimension.

10. The microwave tissue treatment device of claim 8, wherein the proximal region defines a first internal diameter, the intermediate region defines a second internal diameter, and the distal region defines a third internal diameter.

11. The microwave tissue treatment device of claim 10, wherein the first internal diameter is greater than the second internal diameter and the second internal diameter is greater than the third internal diameter.

12. The microwave tissue treatment device of claim 10, wherein at least a portion of the inner conductor defines an arcuate profile when deployed.

13. The microwave tissue treatment device of claim 1, wherein at least a portion of the inner conductor defines a substantially non-arcuate profile when deployed.

14. The microwave tissue treatment device of claim 1, wherein the fluid is selected from the group consisting of water, saline, ammonium chloride, sodium nitrate, and potassium chloride.

15. The microwave tissue treatment device of claim 1, wherein the cooling system further includes at least one pump such that the at least one fluid may be circulated therethrough.

16. An improved microwave tissue treatment device having an antenna assembly that includes an outer conductor and an inner conductor with a dielectric material disposed at least in part therebetween, at least a portion of the inner conductor being deployable from the outer conductor, wherein the improvement comprises:
a sleeve at least partially disposed about a distal portion of the inner conductor and defining at least one cavity, wherein at least a portion of the sleeve is configured to be deployable from within a lumen defined by a distal portion of the outer conductor;

the dielectric material including a distal portion at least partially disposed within the lumen between the sleeve and the distal portion of the outer conductor;

at least one baffle member disposed within the sleeve and defining at least two regions thereof; and a cooling system including at least one inflow member and at least one outflow member, the at least one inflow member and the at least one outflow member being in fluid communication with the at least one cavity.

17. A microwave tissue treatment device, comprising:

an antenna assembly including:

an elongate member defining a longitudinal axis and having proximal and distal ends;

an outer conductor and an inner conductor each disposed within the elongate member and extending along the longitudinal axis, the outer conductor including a distal portion, wherein at least a portion of the inner conductor is configured to be deployable from the distal portion of the outer conductor such that the antenna assembly may transition from a first position to a second position;

a dielectric material disposed at least in part between the outer conductor and the inner conductor; and a sleeve at least partially disposed about a distal portion of the inner conductor and defining at least one cavity, the at least one cavity including a proximal region defining a first internal diameter, an intermediate region defining a second internal diameter, and a distal region defining a third internal diameter, wherein at least a portion of the sleeve is configured to be deployable from a lumen defined by the distal portion of the outer conductor;

the dielectric material including a distal portion at least partially disposed within the lumen between the sleeve and the distal portion of the outer conductor; and a cooling system including at least one inflow member and at least one outflow member, the at least one inflow member and the at least one outflow member being in fluid communication with the at least one cavity defined by the sleeve, the at least one inflow member and the at least one outflow member configured to circulate at least one fluid within the at least one cavity such that at least a portion of the inner conductor is in fluid contact with the at least one fluid.

18. The microwave tissue treatment device of claim 17, wherein the third internal diameter is greater than the first internal diameter and the second internal diameter.

* * * * *